(12) United States Patent
Behnam

(10) Patent No.: US 8,992,965 B2
(45) Date of Patent: Mar. 31, 2015

(54) BONE MATRIX COMPOSITIONS AND METHODS

(75) Inventor: Keyvan Behnam, Red Bank, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1476 days.

(21) Appl. No.: 11/555,608

(22) Filed: Nov. 1, 2006

(65) Prior Publication Data

US 2007/0110820 A1 May 17, 2007

Related U.S. Application Data

(60) Provisional application No. 60/732,675, filed on Nov. 1, 2005.

(51) Int. Cl.
| | | |
|---|---|---|
| A61F 2/00 | (2006.01) | |
| C07K 14/51 | (2006.01) | |
| A61K 35/32 | (2006.01) | |
| A61K 38/01 | (2006.01) | |
| A61K 38/18 | (2006.01) | |
| A61L 27/12 | (2006.01) | |
| A61L 27/36 | (2006.01) | |
| A61L 27/42 | (2006.01) | |
| A61L 27/48 | (2006.01) | |
| A61L 27/54 | (2006.01) | |
| A61F 2/28 | (2006.01) | |
| A61F 2/30 | (2006.01) | |

(52) U.S. Cl.
CPC . *C07K 14/51* (2013.01); *A61F 2/28* (2013.01); *A61F 2002/2817* (2013.01); *A61F 2002/2835* (2013.01); *A61F 2002/30677* (2013.01); *A61K 35/32* (2013.01); *A61K 38/012* (2013.01); *A61K 38/1875* (2013.01); *A61L 27/12* (2013.01); *A61L 27/3608* (2013.01); *A61L 27/365* (2013.01); *A61L 27/3683* (2013.01); *A61L 27/425* (2013.01); *A61L 27/48* (2013.01); *A61L 27/54* (2013.01); *A61L 2300/252* (2013.01); *A61L 2300/414* (2013.01); *A61L 2300/802* (2013.01); *A61F 2310/00359* (2013.01)
USPC ........................ 424/426; 424/549; 530/399

(58) Field of Classification Search
USPC .................. 424/426, 549; 530/399
See application file for complete search history.

(56) References Cited

U.S. PATENT DOCUMENTS

| | | |
|---|---|---|
| 4,172,128 A | 10/1979 | Thiele et al. |
| 4,294,753 A | 10/1981 | Urist |
| 4,394,370 A | 7/1983 | Jefferies |
| 4,430,760 A | 2/1984 | Smestad |
| 4,440,370 A | 4/1984 | Rood |
| 4,440,750 A | 4/1984 | Glowacki et al. |
| 4,455,256 A | 6/1984 | Urist |
| 4,472,840 A | 9/1984 | Jefferies |
| 4,485,097 A | 11/1984 | Bell |
| 4,563,350 A | 1/1986 | Nathan et al. |
| 4,619,989 A | 10/1986 | Urist |
| 4,657,548 A | 4/1987 | Nichols |
| 4,678,470 A | 7/1987 | Nashef et al. |
| 4,743,259 A | 5/1988 | Bolander et al. |
| 4,755,184 A | 7/1988 | Silverberg |
| 4,761,471 A | 8/1988 | Urist |
| 4,774,228 A | 9/1988 | Seyedin et al. |
| 4,774,322 A | 9/1988 | Seyedin et al. |
| 4,787,906 A | 11/1988 | Haris |
| 4,789,663 A | 12/1988 | Wallace et al. |
| 4,789,732 A | 12/1988 | Urist |
| 4,795,804 A | 1/1989 | Urist |
| 4,804,744 A | 2/1989 | Sen |
| 4,810,691 A | 3/1989 | Seyedin et al. |
| 4,843,063 A | 6/1989 | Seyedin et al. |
| 4,902,296 A | 2/1990 | Bolander et al. |
| 5,041,138 A | 8/1991 | Vacanti et al. |
| 5,073,373 A | 12/1991 | O'Leary |
| 5,106,748 A | 4/1992 | Wozney et al. |

(Continued)

FOREIGN PATENT DOCUMENTS

| | | |
|---|---|---|
| DE | 2 253 086 | 9/1974 |
| DE | 693 24 117 T2 | 6/1994 |

(Continued)

OTHER PUBLICATIONS

Ou et al. Tsinghua Sci. Tehcnol. (2002) 7(4): 352-362.*

(Continued)

*Primary Examiner* — Susan Hanley
(74) *Attorney, Agent, or Firm* — Sorell Lenna & Schmidt LLP

(57) ABSTRACT

An osteoinductive composition, corresponding osteoimplants, and methods for making the osteoinductive composition are disclosed. The osteoinductive composition comprises osteoinductive factors, such as may be extracted from demineralized bone, and a carrier. The osteoinductive composition is prepared by providing demineralized bone, extracting osteoinductive factors from the demineralized bone, and adding the extracted osteoinductive factors to a carrier. Further additives such as bioactive agents may be added to the osteoinductive composition. The carrier and osteoinductive factors may form an osteogenic osteoimplant. The osteoimplant, when implanted in a mammalian body, can induce at the locus of the implant the full developmental cascade of endochondral bone formation including vascularization, mineralization, and bone marrow differentiation. Also, in some embodiments, the osteoinductive composition can be used as a delivery device to administer bioactive agents.

7 Claims, No Drawings

(56) References Cited

U.S. PATENT DOCUMENTS

| | | |
|---|---|---|
| 5,166,187 A | 11/1992 | Collombel et al. |
| 5,211,664 A | 5/1993 | Tepic et al. |
| 5,236,456 A | 8/1993 | O'Leary et al. |
| 5,266,683 A | 11/1993 | Oppermann et al. |
| 5,270,300 A | 12/1993 | Hunziker |
| 5,284,655 A | 2/1994 | Bogdansky et al. |
| 5,290,558 A | 3/1994 | O'Leary et al. |
| 5,290,763 A | 3/1994 | Poser et al. |
| 5,314,476 A | 5/1994 | Prewett et al. |
| 5,336,264 A | 8/1994 | Constanz et al. |
| 5,354,557 A | 10/1994 | Oppermann et al. |
| 5,378,469 A | 1/1995 | Kemp et al. |
| 5,385,887 A | 1/1995 | Yim et al. |
| 5,405,390 A | 4/1995 | O'Leary et al. |
| 5,490,962 A | 2/1996 | Cima et al. |
| 5,501,706 A | 3/1996 | Arenberg |
| 5,507,813 A | 4/1996 | Dowd et al. |
| 5,518,680 A | 5/1996 | Cima et al. |
| 5,531,735 A | 7/1996 | Thompson |
| 5,563,124 A | 10/1996 | Damien et al. |
| 5,571,189 A | 11/1996 | Kuslich |
| 5,607,269 A | 3/1997 | Dowd et al. |
| 5,618,339 A | 4/1997 | Ito |
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,291,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zucherman |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1* | 9/2002 | McKay et al. .................. 606/99 |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | Morris et al. |
| 2004/0024457 A1 | 2/2004 | Boyce et al. |
| 2004/0059364 A1 | 3/2004 | Barton et al. |
| 2004/0072322 A1* | 4/2004 | Thorne ......................... 435/226 |
| 2004/0146543 A1 | 7/2004 | Shimp et al. |
| 2004/0220615 A1 | 11/2004 | Lin |
| 2004/0249464 A1 | 12/2004 | Bindseil et al. |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1* | 2/2005 | Damien ......................... 514/21 |
| 2005/0131417 A1 | 6/2005 | Ahern et al. |
| 2005/0244450 A1 | 11/2005 | Reddi |
| 2005/0244457 A1 | 11/2005 | Reddi |
| 2005/0251267 A1 | 11/2005 | Winterbottom et al. |
| 2005/0283255 A1 | 12/2005 | Geremakis et al. |
| 2006/0216321 A1 | 9/2006 | Lyu et al. |
| 2006/0216323 A1 | 9/2006 | Knaack et al. |
| 2006/0287732 A1 | 12/2006 | Pezeshkian |
| 2007/0049731 A1* | 3/2007 | Thorne et al. ................. 530/350 |
| 2007/0073401 A1 | 3/2007 | Pointillart et al. |
| 2007/0093896 A1 | 4/2007 | Malinin |
| 2007/0098756 A1 | 5/2007 | Behnam |
| 2007/0118222 A1 | 5/2007 | Lang |
| 2007/0125700 A1 | 6/2007 | Ding et al. |
| 2007/0142916 A1 | 6/2007 | Olson et al. |
| 2007/0154563 A1 | 7/2007 | Behnam et al. |
| 2007/0162132 A1 | 7/2007 | Messerli |
| 2007/0178158 A1 | 8/2007 | Knaack et al. |
| 2007/0231788 A1 | 10/2007 | Behnam et al. |
| 2008/0027546 A1 | 1/2008 | Semler et al. |
| 2008/0069852 A1 | 3/2008 | Shimp et al. |
| 2008/0091270 A1 | 4/2008 | Miller et al. |
| 2008/0260794 A1 | 10/2008 | Lauritzen et al. |
| 2009/0087471 A1 | 4/2009 | Shimp et al. |
| 2009/0130173 A1 | 5/2009 | Behnam et al. |
| 2009/0155378 A1 | 6/2009 | Behnam et al. |
| 2009/0157087 A1 | 6/2009 | Wei et al. |
| 2009/0192474 A1 | 7/2009 | Wei et al. |
| 2009/0220605 A1 | 9/2009 | Wei et al. |

FOREIGN PATENT DOCUMENTS

| | | |
|---|---|---|
| EP | 0 082 621 | 6/1983 |
| EP | 0 212 474 | 3/1987 |

(56) References Cited

FOREIGN PATENT DOCUMENTS

| | | |
|---|---|---|
| EP | 0309241 A2 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 603 920 A1 | 6/1994 |
| EP | 0 621 020 A1 | 10/1994 |
| EP | 0781564 A2 | 7/1997 |
| JP | 01/179689 | 7/1989 |
| WO | WO 88/00205 | 1/1988 |
| WO | WO 88/01517 | 3/1988 |
| WO | WO 90/03733 | 4/1990 |
| WO | WO 94/21298 | 9/1994 |
| WO | WO 95/31948 | 11/1995 |
| WO | WO 96/39170 | 12/1996 |
| WO | WO 00/13615 | 3/2000 |
| WO | 00/45870 A | 8/2000 |
| WO | WO 00/47736 | 8/2000 |
| WO | WO 01/28461 A2 | 4/2001 |
| WO | WO 01/70136 A2 | 9/2001 |
| WO | WO 01/79342 A2 | 10/2001 |
| WO | WO 02/069818 A2 | 9/2002 |
| WO | WO 03/025271 A1 | 3/2003 |
| WO | WO 03/030956 A3 | 4/2003 |
| WO | WO 2004/073563 A | 9/2004 |
| WO | WO 2005/065396 A2 | 7/2005 |
| WO | WO 2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Ou et al. Eur. J. Biochem. (2001) 268: 5901-5911.*
Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989, 348-353.
Laursen, Malene et al., "Optimal Handling of freshcancellous bone graft—Different peroperative storing techniques evaluated by in vitro osteobalst-like cell metabolism", *Acta Orthop Scand.*, vol. 74, No. 4 2003, 491.
Fujishiro et al., "Histological evaluation of an impacted bone graft substitute composed of a combination of mineralized and demineralized allograft in a sheep vertebral bone defect", *Journal of Biomedical Materials Research Part A*, (2007), pp. 538-544.
Xiaobo, H., et al., "Experimental and Clinical Investigations of Human Insoluble Bone Matrix Gelatin," *Clin. Orthopaedics and Related Research*, vol. 293: 360-365 (1993).
Mellonig, J.T. "Decalcified Freeze-Dried Bone Allograft as an Implant Material in Human Periodontal Defects", *The International Journal of Periodontics and Restorative Dentistry*, 4(6): 40-55 (1984).
Enlow, Donald H., "Principles of Bone Remodeling: An Account of Post-natal Growth and remodeling Processes in Long Bones and the Mandible," Charles C. Thomas, Springfield, Ill., pp. 3-115 (1963).
Katz, "The Biology of Heavy Water," *Scientific American*, vol. 203, pp. 106-116 (1960).
Urist, M.R., "Bone Formation by Autoinduction", *Science*, 150(698):893-9,1965.
Urist, M.R. et al., "The Bone Induction Principle", *Clin. Orthop. Rel. Res.* 53:243-283, 1967.
Glowacki et al., *Calcif. Tissue Int.* 33:71, 1981.
Neigel et al., *Ophthal. Plast. Reconstr. Surg.* 12:108, 1996.
Whiteman et al., *J. Hand. Surg.* 18B:487, 1993.
Schwartz et al., *Acta. Orthop. Scan.* 60(6): 693-695, 1989.
Aspenberg et al., *J. of Orthop. Res.* 9:20-25, 1991.
Caplanis et al., *J. Periodontal*, 851-856, Aug. 1998.
Sampath et al., *Proc. Natl. Acad. Sci.* 84:7,109-7113, 1987.
Urist et al., *Proc. Soc. Exp. Biol.* 173:194-199, 1983.
Canalis et al., *Science*, 210:1021-1023, 1980.
Farley et al., *Biochem*, 21:3508-3513, 1982.
Urist et al., *Prop. Natl. Acad. Sci.* 81:371-375, 1984.
Wang et al., *Proc. Nat. Acad. Sci.* 85:9484-9488,1988.
Wang et al., *Proc. Nat. Acad. Sci.* 87:2220-2224, 1990.
Sampath and Reddi, *Proc. Nat. Acad. Sci.* 80:6591-6594, 1983.
Deatherage et al., *Collagen Rel. Res.* 7:225-231, 1987.
Bolander et al.,"The Use of Demineralized Bone Matrix ion to Repair of Segmental Defects", *The Journal of Bone and Joint Surgery*, vol. 68-A, No. 8, pp. 1264-1273, 1986.
Glowacki et al., "Demineralized Bone Implants", *Symposium on Horizons in Plastic Surgery*, vol. 12, No. 2, pp. 233-241, 1985.
Gepstein et al., "Bridging Large Defects in Bone by Demineralized Bone Matrix in the Form of a Powder", *The Journal of Bone and Joint Surgery*, vol. 69-A, No. 7, pp. 984-991, 1987.
Kaban et al., "Treatment of Jaw Defects with Demineralized Bone Implants", *Journal of Oral and Maxillofacial Surgery*, pp. 623-626, Jun. 6, 1989.
Todescan et al., "A Small Animal Model for Investigating Endosseous Dental Impants:Effect of Graft Materials on Healing of Endoss, Porous-Surfaced Implants Placed in a Fresh Extraction Socket", *The Journal of Oral and Maxillofacial Implants*, vol. 2, No. 2, pp. 217-223, 1987.
Steadman et al., "Microfracture: Surgical Technique and Rehabilitation to Treat Chondral Defects", *Clin. Orthop.*, 391 S:362-369, 2001.
Hunziker et al., "Repair of Partial Thickness Defects in Articulate Cartilage: Cell Recruitment From the Synovial Membrane", *Journal Bone Joint Surg.*, 78-A: 721-733, 1996.
Edwards et al., "Osteoinduction of Human Demineralized Bone: Characterization in a Rat Model", *Clinical Orthopaedics & Rel. Res.* 357:219-228, Dec. 1998.
Dubois et al., *American Journal of Pathology*, 158(1):305-316, 2001.
Cui et al., *The Embo Journal*, 17(16):4735-4743, 1998.
Cui et al., *Genes and Development*, 15:2797-2802, 2001.
Canalis et al., *Endocrine Rev.* 24(2):218-235, 2003.
Reddi et al., *Proc. Natl. Acad. Sci.* 69:1601-1605, 1972.
Lewandrowski et al., *Clin. Ortho. Rel. Res.* 317: 254-262, 1995.
Lewandrowski et al., *J. Biomed. Mater. Res.* 31:365-372, 1996.
Lewandrowski et al., *Calcified Tissue Int.* 61:294-297,1997.
Lewandrowski et al., *I Ortho. Res.* 15:748-756,1997.
Russell et al., *Orthopaedics*, 22(5):524-53, May 1, 1999.
Kasten et al., "Comparison of Human Bone Marrow Stromal Cells Seeded on Calcium-Deficient Hydroxyapatite, Betatricalcium Phosphate and Demineralized Bone Matrix", Biomaterials, 24(15):2593-603, 2003.
van den Ouweland, A.M.W. et al., *Nucl Acid Res.* 18, p. 664,1990.
Steiner, D.F., *Curr. Opinion Chem. Biol.* 2, pp. 31-39, 1998.
Bravo, D.A. et al., *Journal Biol Chem.* 269, pp. 25830-25873, 1994.
Krysan, D.J., et al., *Journal Biol. Chem.* 274, pp. 23229-23234, 1999.
Jean et al., *Proc. Natl. Acad. Sci. USA* 95, pp. 7293-7298, 1998.
Cameron, A. et al., *J. Biol. Chem.* 275, pp. 36741-36749, 2000.
Dubois et al., *American Journal of Pathology* 158 (1):305-316, 2001.
Serini et al., *Nature*, 424:391-397, Jul. 2003.
Aspenberg P. et al., "Bone morphogenetic protein induces bone in the squirrel monkey, but bone matrix does not", *Acta Orthop Scand.* 63(6): 619-22 (Dec. 1992).
Blumenthal et al. "The use of collagen membrane barriers in conjunction with combined demineralized bone-collagen gel implants in human infrabony defects," *J. Periodontal* 61(6): 319-327 (Jun. 1990).
Constantino, et al. "Bone Healing and Bone Substitutes," *Facial Plastic Surgery* 18(1): pp. 14-26 (2002).
Crowe et al., "Inhibition of Enzymatic Digestion of Amylose by Free Fatty Acids in Vitro Contributes to Resistant Starch Formation", *J. Nutr.*, 130(8): 2006-2008 (2000).
Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).
Gamradt, et al. "Bone Graft for Revision Hip Arthroplasty", *Clin. Ortho. and Related Research*, 417: 183-194 (2003).
Glowacki, "Cellular Reactions to Bone-Derived Material," *Clin. Ortho. and Related Research*, 324: 47-54 (1996).
Han B., et al., "Quantitive and sensitive in vitro assay for osteoinductive activity of demineralized bone matrix," *J. Orthop. Res.* 21(4): 648-54 (Jul. 2003).

(56) References Cited

OTHER PUBLICATIONS

Han, C. et al. "Autolysed Antigen-Extracted Allogeneic Boen for Repair of Diaphyseal Boen Defects in Rabbits," *Yonsei Medical Journal*, 31(3): 251-257 (1990).
Hollinger, et al. "A comparison of four particulate bone derivatives," *Clin. Ortho. and Related Research*, 267: 255-263 (Jun. 1991).
Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).
Jain et al., "Anchoring of phospholipase $A_2$: the effect of anions and deuterated water, and the role of N-terminus region," *Biochem. Et Bioph s. Acta*, 860: 448-461 (1986).
Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).
Johnson et al. "Human Bone Mortphogenetic Protein Allografting for Reconstruction of Femoral Nonunion," *Clin. Ortho. and Related Research*, 371: 61-74 (2000).
Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).
Johnson et al. "Resistant Nonunions and Partial or Complete Segmental Defects of Long Bones," *Clin. Ortho. and Related Research*, 277: 229-237 (Apr. 1992).
Kawai et al., *Clin. Orthopaedics and Related Res.*, 233: 262-267 (1988).
Kubler et al. "Allogenic Bone & Cartilage Morphogenesis," *J. Craniomaxillofac. Surg.*, 19(7): 283-288 (1991).
Kubler et al. "Osteoinductive, morphologic, and biomechanical properties of autolyzed, antigen-extracted, allogeneic human bone," *J. Oral Maxillofac Surg*, 51: 1346-1357 (1993).
Kubler et al. "Repair of human skull defects using osteoinductive bone alloimplants," *J. of Cranio Maxillofac. Surg.* 23: 337-346 (1995).
Lee et al., *Nature*, 424: 389 (2003).
Lewandrowski et al. "Mechanical Properties of Perforated and Partially Demineralized Bone Grafts," *Clin. Ortho. and Related Research*, 353: 238-246 (1998).
Lieberman, et al. "Treatment of Osteonecrosis of the Femoral Head with Core Decompression and Human Bone Morphogenetic Protein," *Clin. Ortho. and Related Research*, 429: 139-145 (2004).
Lotz, *Clin. Orthopaedics and Related Res.*, 391S: S108-S115 (2001).
Mellonig, James. "Bone Allografts in Periodontal Therapy," *Clin. Ortho. and Related Research*, 324: 116-125 (1996).
Mellonig, "Decalcified Freeze-dried Bone Allograft as an Implant Material in Human Periodontal Defects," *The Int'l Jour. of Periodontics and Restorative Dentistry*, 4(6): 41-45 (1984).
Miloslav et al., "Autolyzed antigen-extracted allogeneic bone for bridging segmented diaphyseal bone defects in rabbits," *Clinical Orthopaedics and Related Research*, 229: 249-256 (Apr. 1988).
Nade et al. "Decalcified Bone as a Substrate for Osteogenesis," *Bone Joint Surg.* 59(2): 189-1996 (1977).
Nogami et al., "Sustrata Prepared from Bone Matrix for Chondrogenesis in Tissue Culture", *The Journal of Cell Biology*, 62: 510-519 (1974).
Nogami et al., "Transmembrane Bone Matrix Gelatin—Induced Differentiation of Bone", *Calcif. Tiss. Res.*, 19: 153-163 (1975).
Oberg et al. "Bone formation after implantation of autolysed antigen extracted allogeneic bone in ovariectomized rabbits," *Int. J. Oral Maxillofac. Surg.* 32: 628-632 (2003).
Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).
Ousterhout. "Clinical Experience in Cranial and Facial Reconstruction with Demineralized Bone," *Ann. Plast. Surg.* 15(5): 367-373 (1995).
Paralkar et al., "An EP2 receptor-selective prostaglandin $E_2$ agonist induces bone healing," *PNAS*, 100(11): 6736-6740 (2003).
Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).
Ray et al., "Bone Implants," *J. Bone Joint Surgery*, 39A(5): 1119-1128 (1957).
Ripamonti et al. "Bone induction in a composite allogeneic bone/alloplastic implant," J. *Oral Maxillofac. Surg.* 47: 963-969 (1989).
Ripamonti et al. "The induction of bone in osteogenic composites of bone matrix and porous hydroxyapatite replicas: Experimental study on the baboon," *Oral Maxillofac. Surg.* 9: 817-830 (1991).
Ripamonti. "Bone induction in nonhuman primates: an experimental study on the baboon," *Clin. Ortho. and Related Research*, 269: 284-294 (Aug. 1991).
Ripamonti. "Calvarial regeneration in primates with autolyzed antigen-extracted allogeneic bone," *Clin. Ortho. and Related Research*, 282: 293-303 (Sep. 1992).
Ronningen et al. "Bone formation enhanced by induction," *Acta Orthop Scan* 56: 67-71 (1985).
Ronningen et al. "Osteogenesis promoted by bone matrix combined with marrow," *Acta Orthop Scand* 5Z: 15-18 (1986).
Rosenquist et al. "Effects of bone grafting on maxillary bone healing in the growing pig," *J. Oral Maxillofac. Surg.* 40: 566-569 (1982).
Rosenthal et al. "Demineralized bone implants for nonunion fractures, bone cysts, and fibrous lesions," *Clin. Ortho. and Related Research* 362: 61-69 (1999).
Sailer et al. "Application of purified bone morphogenetic protein (BMP) in cranio-maxillo-facial surgery," *Jour. of Cranio-Maxillo-Facial Surgery* 22: 2-11 (1994).
Sampath et al., "Bovine osteogenic protein is composed of dimmers of OP-1 and BMP-2A, Two members of the transforming growth factor-beta superfamily," *J. Biol. Chem.*, 5:265(22): pp. 13198-13205 (Aug. 1990).
Schmid et al. "Osteoinduction in tibial defects in the dog," *Unfallchirurgie* 19: 1-8 (1993).
Schwarz et al. "Decalcified and undecalcified cancellous bone block implants do not heal diaphyseal defects in dogs," *Arch. Orthop. Trauma Surg.* 111:47-50 (1991).
Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).
Terashima et al., Chondrogenesis in Outgrowths of Muscle Tissue onto Modified Bone Matrix in Tissue Culture, *Clinical Orthopaedics and Related Research*, 127: 248-256 (Sep. 1977).
Toriumi et al. "Demineralized Bone," Arch Otolaryngol Head Neck Surg. 116: 676-680 (Jun. 1990).
Ueland et al., *J. Clin. Endocrinol. & Metab.*, 84(1): 123-127 (1999).
Urist et al., "Bone morphogenesis in Implants of Insoluble Bone Gelatin," *Proc. Natl. Acad. Sci.*, , 70(12): 3511-5 (Dec. 1973).
Urist et al., ., "Preservation and biodegradation of the morphogenetic property of bone matrix," *J. Theor. Biol.* 38: 155-67 (1973).
Urist et al., "Observations implicating an extracellular enzymic mechanism of control of bone morphogenesis," *J. Histochem & Cytochem*, 22(2): 88-103 (1974).
Urist et al., "A Chemosterilized Antigen-Extracted Autodigested Alloimplant for Bone Banks," *Arch Surg.* vol. 110: 416-428 (Apr. 1975).
Urist et al., "Cartilage Tissue Differentiation from Mesenchymal Cells Derived from Mature Muscle in Tissue Culture", In Vitro, 14(8): 697-706 (1978).
Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).
Van den Berg et al., "Tissue Engineering, Cells, Scaffolds, and Growth Factors," *Clin. Orthopaedics and Related Res.*, 391S: S244-S250 (2001).
White et al., "Effective terminal sterilization using supercritical carbon dioxide," *Journal of Biotechnology*, 123: 504-515 (2006).

(56) References Cited

OTHER PUBLICATIONS

Whittaker et al., "Matrix Metalloproteinases and Their Inhibitors—Current Status and Future Challenges," *Celltransmissions*, 17(1): 3-14.

Xiaobo et al., "Experimental and Clinical Investigations of Human Insoluble Bone Matrix Gelatin," *Clin. Orthopaedics and Related Research*, 293: 360-365 (1993).

Young et al. "Morphological changes of autoclaved autogenic bone implantation and autoclaved autogenic bone supplemented with allogenic demineralized bone matrix in rat parietal bone," *Histol Histopathol*. 11: 361-369 (1996).

Zhang et al., "A Quantitative assessment of osteoinductivity of human demineralized bone matrix," *J. Periodontal*, 68(11): 1076-84 (Nov. 1997).

\* cited by examiner

BONE MATRIX COMPOSITIONS AND METHODS

CROSS-REFERENCE TO RELATED APPLICATION

This application claims the benefit of U.S. Provisional Application No. 60/732,675, filed on Nov. 1, 2005, the content of which is incorporated in its entirety by reference herein.

BACKGROUND

Introduction

Mammalian bone tissue is known to contain one or more proteinaceous materials, presumably active during growth and natural bone healing, that can induce a developmental cascade of cellular events resulting in endochondral bone formation. The active factors are variously been referred to in the literature as bone morphogenetic or morphogenic proteins (BMPs), bone inductive proteins, bone growth or growth factors, osteogenic proteins, or osteoinductive proteins. These active factors are collectively referred to herein as osteoinductive factors.

It is well known that bone contains these osteoinductive factors. These osteoinductive factors are present within the compound structure of cortical bone and are present at very low concentrations, e.g., 0.003%. Osteoinductive factors direct the differentiation of pluripotential mesenchymal cells into osteoprogenitor cells that form osteoblasts. Based upon the work of Marshall Urist as shown in U.S. Pat. No. 4,294,753, issued Oct. 13, 1981, proper demineralization of cortical bone exposes the osteoinductive factors, rendering it osteoinductive, as discussed more fully below.

Overview of Bone Grafts

The rapid and effective repair of bone defects caused by injury, disease, wounds, or surgery has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB") long has been considered the gold standard for bone grafts. ACB is osteoinductive and nonimmunogenic, and, by definition, it has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification and development of alternative bone graft materials. Urist has published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. As mentioned above, DBM is an osteoinductive material, in that it induces bone growth when implanted in an ectopic site of a rodent, owing to the osteoinductive factors contained within the DBM. Honsawek et al. (2000). It is now known that there are numerous osteoinductive factors, e.g., BMP 1-15, which are part of the transforming growth factor-beta (TGF-beta) superfamily (Kawabata et al., 2000). BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta. 1) (Hauschka, et al. 1986; Canalis, et al, 1988; Mohan et al. 1996).

DBM implants have been reported to be particularly useful (see, for example, U.S. Pat. Nos. 4,394,370, 4,440,750, 4,485,097, 4,678,470, and 4,743,259; Mulliken et al., Calcif Tissue Int. 33:71, 1981; Neigel et al., Opthal. Plast. Reconstr. Surg. 12:108, 1996; Whiteman et al., J. Hand. Surg. 18B:487, 1993; Xiaobo et al., Clin. Orthop. 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

Some studies indicate that the osteoinductive capabilities of demineralized bone from higher order species in higher order species is relatively low. One study compared the osteoinductivity of rat and canine bone matrix, and of cortical and cancellous bone. Rat bone matrix consistently induced new bone and high phosphatase levels when implanted ectopically in rat. Canine matrix induced small amounts of bone and lower phosphatase levels when implanted in dog and in rat, with cortical matrix being somewhat more inductive than cancellous matrix. Demineralized cancellous bone matrix from dog was the only material tested not showing any osteoinductivity. Schwarz et al., Acta. Orthop. Scan. 60(6): 693-695, 1989.

Similarly, another study determined that monkey bone matrix induces ectopic bone formation in the athymic rat but not in adult monkeys. It was concluded that adult monkey bone matrix contains bone inductive properties but that these properties are not sufficient to induce bone formation in adult monkey muscle sites. Aspenberg et al., J. of Orthop. Res. 9:20-25, 1991.

Yet another study evaluated bone and cementum regeneration following guided tissue regeneration (GTR) in periodontal fenestration defects. Specifically, the adjunctive effect of allogenic, freeze-dried DBM implant was evaluated and found to exhibit no discernible adjunctive effect to GTR in the defect model. The critical findings were 1) the DBM particles remained embedded in dense connective tissue without evidence of bone metabolic activity; and 2) limited and similar amounts of bone and cementum regeneration were observed for both GTR plus DBM and GTR defects. Caplanis et al., J Periodontal 851-856, August, 1998.

Current DBM formulations have various drawbacks. First, while the collagen-based matrix of DBM is relatively stable, the osteoinductive factors within the DBM matrix are rapidly degraded. The osteogenic activity of the DBM may be significantly degraded within 24 hours after implantation, and in some instances the osteogenic activity may be inactivated within 6 hours. Therefore, the osteoinductive factors associated with the DBM are only available to recruit cells to the site of injury for a short time after transplantation. For much of the healing process, which may take weeks to months, the implanted material may provide little or no assistance in recruiting cells. In addition to the osteoinductive factors present within the DBM, the overall structure of the DBM implant is also believed to contribute to the bone healing capabilities of the implant.

Extracting Proteins

The potential utility of osteoinductive factors has been recognized widely. It has been contemplated that the availability of osteoinductive factors could revolutionize orthopedic medicine and certain types of plastic surgery, dental, and various periodontal and craniofacial reconstructive procedures.

Urist's U.S. Pat. No. 4,294,753, herein incorporated by reference, was the first of his many patents on a process for extracting BMP from DBM. At the time of the Urist '753 patent, BMP was referred to generally. However, as mentioned above, now it is known that there are multiple forms of BMP. The Urist process became widely adopted, and though different users may use different chemical agents from those disclosed in the basic Urist process, the basic layout of the steps of the process remains widely used today as one of the main methods of extracting BMP from DBM. See, e.g., U.S. Pub 2003/0065392 (2003); U.S. Pub 2002/0197297 (2002). Urist reported that his basic process actually results in generally low yields of BMP per unit weight of DBM. Urist et al. (1982).

The observed properties of osteoinductive factors have induced an intense research effort in several laboratories directed to isolating and identifying the pure factor or factors responsible for osteogenic activity. A modified process for purification of osteogenic protein from mammalian bone is disclosed by Sampath et al. (1987) Proc. Natl. Acad. Sci. USA 84:7109-7113. Urist et al. (1983), Proc. Soc. Exp. Biol. Med. 173:194-199, disclose a human osteogenic protein fraction which was extracted from demineralized cortical bone by means of a calcium chloride-urea inorganic-organic solvent mixture, and retrieved by differential precipitation in guanidine-hydrochloride and preparative gel electrophoresis. The authors report that the protein fraction has an amino acid composition of an acidic polypeptide and a molecular weight in a range of 17-18 kDa. This material was said to be distinct from a protein called "bone derived growth factor" disclosed by Canalis et al. (1980 Science 210:1021-1023) and by Farley et al. (1982) Biochem 21:3508-3513.

Urist et al., (1984) Proc. Natl. Acad. Sci. USA 81:371-375, disclose a bovine BMP extract having the properties of an acidic polypeptide and a molecular weight of approximately 18 kDa. The authors report that the protein was present in a fraction separated by hydroxyapatite chromatography, and that it induced bone formation in mouse hindquarter muscle and bone regeneration in trephine defects in rat and dog skulls. Their method of obtaining the extract from bone results in ill-defined and impure preparations.

European Patent Application Serial No. 148,155, published Oct. 7, 1985, herein incorporated by reference, purports to disclose osteogenic proteins derived from bovine, porcine, and human origin. One of the proteins, designated by the inventors as a P3 protein having a molecular weight of 22-24 kDa, is said to have been purified to an essentially homogeneous state. This material is reported to induce bone formation when implanted into animals.

International Application No. PCT/087/01537 (Int. Pub. No. WO88/00205) discloses an impure fraction from bovine bone with bone induction qualities. The named applicants also disclose putative "bone inductive factors" produced by recombinant DNA techniques. Four DNA sequences were retrieved from human or bovine genomic or cDNA libraries and expressed in recombinant host cells. While the applicants stated that the expressed proteins may be bone morphogenic proteins, bone induction was not demonstrated. This same group reported subsequently ((1988) Science 242:1528-1534) that three of the four factors induce cartilage formation, and postulate that bone formation activity "is due to a mixture of regulatory molecules" and that "bone formation is most likely controlled . . . by the interaction of these molecules." Again, no bone induction was attributed to the products of expression of the cDNAs. See also Urist et al., EPO 0,212, 474, entitled "Bone Morphogenic Agents."

Wang et al., (1988) Proc. Nat. Acad. Sci. USA 85: 9484-9488, disclose the partial purification of a bovine bone morphogenetic protein from guanidine extracts of demineralized bone having cartilage and bone formation activity as a basic protein corresponding to a molecular weight of 30 kDa determined from gel elution. Separation of the 30 kDa fraction yielded proteins of 30, 18, and 16 kDa, which, upon separation, were inactive. In view of this result, the authors acknowledge that the exact identity of the active material had not been determined.

Wang et al., (1990) Proc. Nat. Acad. Sci. USA 87: 2220-2224, describe the expression and partial purification of one of the cDNA sequences described in PCT 87/01537. Consistent cartilage and/or bone formation with their protein requires a minimum of 600 ng of 50% pure material.

International Application No. PCT/89/04458 (Int. Pub. No. WO90/003733) describes the purification and analysis of a family of osteogenic factors called "P3 OF 31-34.". The protein family contains at least four proteins, which are characterized by peptide fragment sequences. The impure mixture P3° F. 31-34 is assayed for osteogenic activity. The activity of the individual proteins is neither assessed nor discussed.

Implanting Extracted Proteins

Successful implantation of the osteoinductive factors for endochondral bone formation requires association of the proteins with a suitable carrier material capable of maintaining the proteins at an in vivo site of application. The carrier should be biocompatible, in vivo biodegradable, and porous enough to allow cell infiltration. Insoluble collagen particles that remain after guanidine extraction and delipidation of pulverized bone generally have been found effective in allogenic implants in some species. However, studies have shown that while osteoinductive proteins are useful cross species, the collagenous bone matrix generally used for inducing endochondral bone formation is species-specific. Sampath and Reddi, (1983) Proc. Nat. Acad. Sci. USA 80: 6591-6594. Demineralized, delipidated, extracted xenogenic bone matrix carriers implanted in vivo invariably fail to induce osteogenesis, presumably due to inhibitory or immunogenic components in the bone matrix. Even the use of allogenic bone matrix in osteogenic devices may not be sufficient for osteoinductive bone formation in many species, as discussed above.

U.S. Pat. No. 4,563,350, herein incorporated by reference, discloses the use of trypsinized bovine bone matrix as a xenogenic matrix to effect osteogenic activity when implanted with extracted, partially purified bone-inducing protein preparations. Bone formation is said to require the presence of at least 5%, and preferably at least 10%, non-fibrillar collagen. The named inventors claim that removal of telopeptides that are responsible in part for the immunogenicity of collagen preparations is more suitable for xenogenic implants.

European Patent Application Serial No. 309,241, published Mar. 29, 1989, herein incorporated by reference, discloses a device for inducing endochondral bone formation comprising an osteogenic protein preparation, and a matrix carrier comprising 60-98% of either mineral component or bone collagen powder and 2-40% atelopeptide hypoimmunogenic collagen.

Deatherage et al., (1987) Collagen Rel. Res. 7: 2225-2231, purport to disclose an apparently xenogenic implantable device comprising a bovine bone matrix extract that has been minimally purified by a one-step ion exchange column and reconstituted with highly purified human Type-I placental collagen.

U.S. Pat. No. 3,394,370, herein incorporated by reference, describes a matrix of reconstituted collagen purportedly useful in xenogenic implants. The collagen fibers are treated enzymatically to remove potentially immunogenic telopeptides (also the primary source of interfibril crosslinks), and are dissolved to remove associated noncollagenenous components. The matrix is formulated by dispersing the reconstituted collagen in acetic acid to form a disordered matrix of elementary collagen molecules that is then mixed with an osteogenic substance and lyophilized to form a "semi-rigid foam or sponge" that is preferably crosslinked. The formulated matrix is not tested in vivo.

U.S. Pat. No. 4,172,128, herein incorporated by reference, describes a method for degrading and regenerating bone-like material of reduced immunogenicity, said to be useful cross-species. Demineralized bone particles are treated with a swelling agent to dissolve any associated mucopolysaccharides (glycosaminoglycans), and the collagen fibers subsequently dissolved to form a homogenous colloidal solution. A gel of reconstituted fibers then can be formed using physiologically inert mucopolysaccharides and an electrolyte to aid in fibril formation.

The use of pulverized exogenous bone growth material, e.g., derived from demineralized allogenic or xenogenic bone, in the surgical repair or reconstruction of defective or diseased bone is known. See, in this regard, the disclosures of U.S. Pat. Nos. 4,394,370, 4,440,750, 4,472,840, 4,485,097, 4,678,470, and 4,743,259; Bolander et al., "The Use of Demineralized Bone Matrix in the Repair of Segmental Defects," The Journal of Bone and Joint Surgery, Vol. 68-A, No. 8, pp. 1264-1273; Glowacki et al, "Demineralized Bone Implants," Symposium on Horizons in Plastic Surgery, Vol. 12, No. 2; pp. 233-241 (1985); Gepstein et al., "Bridging Large Defects in Bone by Demineralized Bone Matrix in the Form of a Powder," The Journal of Bone and Joint Surgery, Vol. 69-A, No. 7, pp. 984-991 (1987); Mellonig, "Decalcified Freeze-Dried Bone Allograft as an Implant Material In Human Periodontal Defects," The International Journal of Periodontics and Restorative Dentistry, pp. 41-45 (June 1984); Kaban et al., "Treatment of Jaw Defects with Demineralized Bone Implants," Journal of Oral and Maxillofacial Surgery, pp. 623-626 (Jun. 6, 1989); and Todescan et al., "A Small Animal Model for Investigating Endosseous Dental Implants: Effect of Graft Materials on Healing of Endosseous, Porous-Surfaced Implants Placed in a Fresh Extraction Socket," The International Journal of Oral & Maxillofacial Implants Vol. 2, No. 4, pp. 217-223 (1987), all herein incorporated by reference.

A variety of approaches have been explored in an attempt to recruit progenitor cells or chondrocytes into an osteochondral or chondral defect. For example, penetration of subchondral bone has been performed in order to access mesenchymal stem cells (MSCs) in the bone marrow, which have the potential to differentiate into cartilage and bone. Steadman, et al., "Microfracture: Surgical Technique and Rehabilitation to Treat Chondral Defects," *Clin. Orthop.*, 391 S:362-369 (2001). In addition, some factors in the body are believed to aid in the repair of cartilage. For example, transforming growth factors beta (TGF-8) have the capacity to recruit progenitor cells into a chondral defect from the synovium or elsewhere when loaded in the defect. Hunziker, et al., "Repair of Partial Thickness Defects in Articular Cartilage: Cell Recruitment From the Synovial Membrane," *J Bone Joint Surg.*, 78-A:721-733 (1996). However, the application of growth factors to bone and cartilage implants has not resulted in the expected increase in osteoinductive or chondrogenic activity.

Each of U.S. Pat. Nos. 5,270,300 and 5,041,138, each herein incorporated by reference, describes a method for treating defects or lesions in cartilage that provides a matrix, possibly composed of collagen, with pores large enough to allow cell population and contain growth factors (TGF-$\beta$ or other factors (such as angiogenesis factors)) appropriate for the type of tissue desired to be regenerated.

U.S. Patent Publication No. 2003/0044445, herein incorporated by reference, describes an osteogenic composition prepared by a process including the steps of subjecting demineralized bone to an extraction medium to produce an insoluble extraction product and a soluble extraction product, separating the insoluble extraction product and the soluble extraction product, drying the soluble extraction product to remove all or substantially all of the moisture in the soluble extraction product, and combining the dried soluble extraction product with demineralized bone particles. This process involves several steps and is quite laborious. Studies using the process have shown that the formed osteogenic composition does not have appreciably increased osteoinductive properties when compared to the demineralized bone particles to which the dried soluble extraction product is added. It was further determined that the demineralized bone from which the extraction products are extracted does not exhibit appreciably decreased osteoinductive properties when compared with its properties prior to extraction. It is thus theorized that the extraction process withdraws only a small fraction of available tissue repair factors.

Overall, current bone and cartilage graft formulations have various drawbacks. The osteoinductive factors within the matrices can be rapidly degraded and, thus, factors associated with the matrix are only available to recruit cells to the site of injury for a short time after implantation. Further, when added to a matrix, the active factors often do not appreciably increase the osteoinductive activity of the matrix or, at least, do not increase the osteoinductive activity of the matrix as much as is desirable.

Thus, it would be useful to provide increased osteoinductive activity from an osteogenic composition in more concentrated form such that increased osteoinductive activity can be seen even with little bone void space.

BRIEF SUMMARY

Osteoinductive compositions, and implants and methods for their production, are provided. According to certain embodiments, a carrier is exposed to a treatment or condition that increases at least one biological activity of the carrier. More specifically, osteoinductive factors are added to the carrier. The biological activities that may be increased include, but are not limited to, bone forming; bone healing; osteoinductive activity, osteogenic activity, chondrogenic activity, wound healing activity, neurogenic activity, contraction-inducing activity, mitosisinducing activity, differentiation-inducing activity, chemotactic activity, angiogenic or vasculogenic activity, and exocytosis or endocytosis-inducing activity.

Thus, an osteoinductive composition is provided comprising osteoinductive factors, such as may be extracted from demineralized bone, and a carrier. The osteoinductive composition provides concentrated or enhanced osteoinductive activity. The osteoinductive composition is prepared by providing demineralized bone, extracting osteoinductive factors from the demineralized bone, and adding the extracted osteoinductive factors to a carrier. The carrier and osteoinductive factors may form an osteogenic osteoimplant. The osteoimplant, when implanted in a mammalian body, can induce at the locus of the implant the full developmental cascade of endochondral bone formation including vascularization, mineralization, and bone marrow differentiation. Also, in some embodiments, the osteoinductive composition can be used as a delivery device to administer additional bioactive agents.

The demineralized bone from which the osteoinductive factors are extracted may be provided in any suitable manner. In a one demineralization procedure, the bone is subjected to an acid demineralization step followed by a defatting/disinfecting step.

A simple and economically viable method for extracting osteoinductive factors from bone is provided herein. The method comprises extracting osteoinductive factors such as noncollagenous proteins (including osteogenic growth factors) from demineralized bone matrix using a chaotropic solvent (e.g., 4M guanidine hydrochloride) or a detergent (e.g., 1% sodium dodecylsulfate), removing the chemical used for extraction in an efficient manner that preserves the biological activity of the growth factors, concentrating the biologically active components by purifying away nonessential proteins and inhibitors of bone morphogenetic protein, and combining the protein extracts with a biologically compatible delivery vehicle. Optionally, methods and materials for the preservation of activity during storage may be utilized with the present invention. Alternate methods of extracting osteoinductive factors from bone may be used.

Thus, the extracted osteoinductive factors are added to a carrier. When the osteoinductive factors are added to a carrier, the carrier acts as a scaffold and aids in controlling release kinetics. Any suitable shape, size, and porosity of carrier may be used. Suitable carriers include demineralized bone; surface demineralized bone; mineralized bone; cancellous scaffolds (mineralized or demineralized); particulate, demineralized, guanidine extracted, species-specific (allogenic) bone; specially treated particulate, calcium phosphates, fatty acids, protein extracted, demineralized, xenogenic bone; collagen; synthetic hydroxyapatites; polymers; hydrogels; starches; polyethylene glycol, tricalcium phosphate, sintered hydroxyapatite, settable hydroxyapatite; polylactic acid; tyrosine polycarbonate; calcium sulfate; collagen sheets; settable calcium phosphate; settable polymers; polymeric cements; settable poly vinyl alcohols; polyurethanes; and other biocompatible settable materials. Further, the carrier may comprise combinations, modifications, or derivatives of these or others. Optionally, xenogenic bone powder carriers also may be treated with proteases such as trypsin. The osteoinductive factors and carrier (or delivery or support system) together form an osteoimplant useful in clinical applications.

Any suitable method for adding, or dispersing, the osteoinductive factors to the carrier may be used. Exactly how this occurs can influence on the biological activity of the final formulation. The extracted osteoinductive factors may have been lyophilized, resulting in a powder composition. For obvious reasons, adding a powder to a bone matrix may be challenging. Thus, it may be desirable to process the osteoinductive factors to form a homogenous mixture that may be more easily added to a carrier. This can have a significant impact on the release kinetics of the osteoinductive factors.

Optionally, other additives may be included in the osteoinductive composition. For example, radiopaque substances, angiogenesis promoting materials, cytokine inhibitors, bioactive agents, other medically/surgically useful substances, binding agents, or other osteoinducing agents may be added The thus formed osteogenic osteoimplant is intended to be applied at a bone repair site, or a site for bone augmentation or ectopic bone formation (e.g., lateral spine fusion). Examples include a site resulting from injury, defect brought about during the course of surgery, infection, malignancy or developmental malformation. The osteoinductive compositions may also be used as drug delivery devices.

This application refers to various patents, patent applications, journal articles, and other publications, all of which are incorporated herein by reference. The following documents are incorporated herein by reference: PCT/US04/43999; PCT/US05/003092; U.S. 2003/0143258 A1; PCT/US02/32941; *Current Protocols in Molecular Biology, Current Protocols in Immunology, Current Protocols in Protein Science, and Current Protocols in Cell Biology*, John Wiley & Sons, N.Y., edition as of July 2002; Sambrook, Russell, and Sambrook, *Molecular Cloning: A Laboratory Manual*, 3rd ed., Cold Spring Harbor Laboratory Press, Cold Spring Harbor, 2001; Rodd 1989 "Chemistry of Carbon Compounds," vols. 1-5 and supps, Elsevier Science Publishers, 1989; "Organic Reactions," vols 1-40, John Wiley and Sons, New York, N.Y., 1991; March 2001, "Advanced Organic Chemistry," 5th ed. John Wiley and Sons, New York, N.Y. In the event of a conflict between the specification and any of the incorporated references, the specification shall control. Where numerical values herein are expressed as a range, endpoints are included.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

DEFINITIONS

Bioactive Agent or Bioactive Compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

Biocompatible, as used herein, is intended to describe materials that, upon administration in vivo, do not induce undesirable long-term effects.

Bone as used herein refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Osteoconductive is used herein to refer to the ability of a nonosteoinductive substance to serve as a suitable template or substance along which bone may grow.

Osteogenic is used herein to refer to the ability of an agent, material, or implant to enhance or accelerate the growth of new bone tissue by one or more mechanisms such as osteogenesis, osteoconduction, and/or osteoinduction.

Osteoimplant as used herein refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.,* 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later timepoints such as 40, 60, or even 100 days following implantation. Percentage of osteoinductivity refers to an osteoinductivity score at a given time point expressed as a percentage of activity, of a specified reference score.

Proteases, as used herein, are protein-cleaving enzymes that cleave peptide bonds that link amino acids in protein molecules to generate peptides and protein fragments. A large collection of proteases and protease families has been identified. Some exemplary proteases include serine proteases, aspartyl proteases, acid proteases, alkaline proteases, metalloproteases, carboxypeptidase, aminopeptidase, cysteine protease, collagenase, etc. An exemplary family of proteases is the proprotein convertase family, which includes furin. Dubois et al., *American Journal of Pathology* (2001) 158(1): 305316. Members of the proprotein convertase family of proteases are known to proteolytically process proTGFs and proBMPs to their active mature forms. Dubois et al., *American Journal of Pathology* (2001) 158(1):305-316; Cui et al., *The Embo Journal* (1998) 17(16):4735-4743; Cui et al., *Genes & Development* (2001) 15:2797-2802, each incorporated by reference herein.

Protease inhibitors, as used herein, refers to chemical compounds capable of inhibiting the enzymatic activity of protein cleaving enzymes (i.e., proteases). The proteases inhibited by these compounds include serine proteases, acid proteases, metalloproteases (examples of some matrix metalloprotease inhibitors are shown in FIG. 6), carboxypeptidase, aminopeptidase, cysteine protease, etc. The protease inhibitor may act specifically to inhibit only a specific protease or class of proteases, or it may act more generally by inhibiting most if not all proteases. Preferred protease inhibitors are protein or peptide based and are commercially available from chemical companies such as Aldrich-Sigma. Protein or peptide-based inhibitors which adhere to the DBM (or calcium phosphate or ceramic carrier) are particularly preferred as they remain associated with the matrix providing a stabilizing effect for a longer period of time than freely diffusible inhibitors. Examples of protease inhibitors include aprotinin, 4-(2aminoethyl)benzenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2macroglobulin, phenylmethylsulfonyl fluo4de (PMSF), pepstatin A, phebestin, 1,10phenanthroline, phosphoramidon, chymostatin, benzamidine HCl, antipain, epsilon aminocaproic acid, N-ethylmaleimide, trypsin inhibitor, 1-chloro-3-tosylamido-7-amino2-heptanone (TLCK), 1-chloro-3-tosylamido-4-phenyl-2-butanone (TPCK), trypsin inhibitor, and sodium EDTA. Stabilizing agent is any chemical entity that, when included in an inventive composition comprising DBM and/or a growth factor, enhances the osteoinductivity of the composition as measured against a specified reference sample. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the inventive composition as compared with an otherwise identical composition lacking the stabilizing agent, or by prolonging or delaying the release of an active factor. In certain embodiments, the stabilizing agent may act by providing a barrier between proteases and sugar-degrading enzymes thereby protecting the osteoinductive factors found in or on the matrix from degradation and/or release. In other embodiments, the stabilizing agent may be a chemical compound that inhibits the activity of proteases or sugar-degrading enzymes. In a preferred embodiment, the stabilizing agent retards the access of enzymes known to release and solubilize the active factors. Half-life may be determined by immunolgical or enzymatic assay of a specific factor, either as attached to the matrix or extracted there from. Alternatively, measurement of an increase in osteoinductivity half-life, or measurement of the enhanced appearance of products of the osteoinductive process (e.g., bone, cartilage or osteogenic cells, products or indicators thereof) is a useful indicator of stabilizing effects for an enhanced osteoinductive matrix composition. The measurement of prolonged or delayed appearance of a strong osteoinductive response will generally be indicative of an increase in stability of a factor coupled with a delayed unmasking of the factor activity.

Superficially demineralized as used herein refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

I. Introduction

The present invention provides osteoinductive compositions and implants and methods for their production. According to certain embodiments, a carrier is exposed to a treatment or condition that increases at least one biological activity of the carrier, as described above. In certain embodiments, the carrier contains peptides or protein fragments that increase the osteoinductive or chondrogenic properties of the carrier. Those of ordinary skill will appreciate that a variety of embodiments or versions of the invention are not specifically discussed below but are nonetheless within the scope of the present invention, as defined by the appended claims.

Bone is made up principally of cells, and also of collagen, minerals, and other noncollagenous proteins. Bone matrices can be nondemineralized, partially demineralized, demineralized, deorganified, anorganic, or mixtures of these. DBM is comprised principally of proteins and glycoproteins, collagen being the primary protein component of DBM. While collagen is relatively stable, normally being degraded only by the relatively rare collagenase enzymes, various other proteins and active factors present in DBM are quickly degraded by enzymes present in the host. These host-derived enzymes include proteases and sugar-degrading enzymes (e.g., endo- and exoglycosidases, glycanases, glycolases, amylase, pectinases, galacatosidases, etc.). Many of the active growth factors responsible for the osteoinductive activity of DBM exist in cryptic form, in the matrix until activated. Activation can involve the change of a pre or pro function of the factor, or release of the function from a second factor or entity that binds to the first growth factor. Thus, growth factor proteins in a DBM or added to a DBM may have a limited osteoinductive effect because they are rapidly inactivated by the proteolytic environment of the implant site, or even within the DBM itself.

A number of endogenous factors that play important roles in the development and/or repair of bone and/or cartilage have been identified. BMPs such as BMP-2 and BMP-4 induce differentiation of mesenchymal cells towards cells of the osteoblastic lineage, thereby increasing the pool of mature cells, and also enhance the functions characteristic of differentiated osteoblasts. Canalis et al., *Endocrine Rev.* 24(2):218-235, 2003. In addition, BMPs induce endochondral ossification and chondrogenesis. BMPs act by binding to specific receptors, which results in phosphorylation of a class of proteins referred to as SMADs. Activated SMADs enter the nucleus, where they regulate transcription of particular target genes. BMPs also activate SMAD-independent pathways such as those involving Ras/MAPK signaling. Unlike most BMPs such as BMP-2 and BMP-4, certain BMPs (e.g., BMP-3) act as negative regulators (inhibitors) of osteogenesis. In addition, BMP-1 is distinct both structurally and in terms of its mechanism of action from other BMPs, which are members of the TGF-β superfamily. Unlike certain other BMPs (e.g., BMP-2, BMP-4), BMP-1 is not osteoinductive. Instead, BMP-1 is a collagenolytic protein that has also been shown to cleave chordin (an endogenous inhibitor of BMP-2 and BMP-4). Tolloid is a metalloprotease that is structurally related to BMP-1 and has proteolytic activity towards chordin. See Canalis, supra, for further details regarding the activities of BMPs and their roles in osteogenesis and chondrogenesis.

A variety of endogenous inhibitors of BMPs have been discovered in addition to chordin. These proteins act as BMP antagonists and include pseudoreceptors (e.g., Bambi) that compete with signaling receptors, inhibitory SMADs that block signaling, intracellular binding proteins that bind to activating SMADs, factors that induce ubiquitination and proteolysis of activating SMADs, and extracellular proteins that bind BMPs and prevent their binding to signaling receptors. Among the extracellular proteins are noggin, chordin, follistatin, members of the Dan/Cerberus family, and twisted gastrulation. These proteins and their sequences are known and readily available to one of ordinary skill in the art.

II. Increasing the Biological Activity of a Carrier

Methods for increasing the biologic activity of a bone, cartilage, or other carrier are provided. Osteoinductive osteoimplants are further provided. The osteoinductive osteoimplants comprise carriers and osteoinductive factors, wherein the carrier has increased biological activity relative to a carrier that has not been exposed to a treatment or condition. The biological activities that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, and exocytosis or endocytosis-inducing activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

An osteoinductive composition is provided comprising osteoinductive factors, such as may be extracted from demineralized bone, and a carrier. The osteoinductive composition provides concentrated or enhanced osteoinductive activity. The osteoinductive composition is prepared by providing demineralized bone, extracting osteoinductive factors from the demineralized bone, and adding the extracted osteoinductive factors to a carrier. The carrier and osteoinductive factors may form an osteogenic osteoimplant. The osteoimplant, when implanted in a mammalian body, can induce at the locus of the implant the full developmental cascade of endochondral bone formation including vascularization, mineralization, and bone marrow differentiation. Also, in some embodiments, the osteoinductive composition can be used as a delivery device to administer bioactive agents.

In certain embodiments, the carrier contains peptides or protein fragments that increase its osteoinductive or chondrogenic properties. The peptides or protein fragments may be exogenously added to the carrier. Further, other agents may be added to the carrier, e.g., agents that improve the osteogenic and/or chondrogenic activity of the matrix by either transcriptional or post-transcriptional regulation of the synthesis of bone or cartilage enhancing or inhibiting factors by cells within the carrier.

III. Provide Demineralized Bone

The demineralized bone from which the osteoinductive factors are extracted may be provided in any suitable manner. The bone useful in the invention herein is obtained utilizing methods well known in the art, e.g., allogenic donor bone. Bone-derived elements can be readily obtained from donor bone by various suitable methods, e.g., as described in U.S. Pat. No. 6,616,698, incorporated herein by reference. The bone may be cortical, cancellous, or cortico-cancellous of autogenous, allogenic, xenogenic, or transgenic origin.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the bone is subjected to an acid demineralization step followed by a defatting/disinfecting step. The bone is immersed in acid over time to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol.

IV. Extract Osteoinductive Factors from DBM

A simple and economically viable method for extracting osteoinductive factors from bone is provided herein. The method comprises extracting osteoinductive factors such as noncollagenous proteins (including osteogenic growth factors) from DBM using a chaotropic solvent or a detergent. The chaotropic solvent may be guanidine hydrochloride of any suitable concentration, such as 4M. The detergent may be sodium dodecylsulfate in any suitable concentration, such as 1%. The chemical used for extraction is removed in an efficient manner that preserves the biological activity of the growth factors. The biologically active components are concentrated by purifying away nonessential proteins and inhibitors of bone morphogenetic protein, and the protein extracts are then combined with a biologically compatible delivery vehicle.

Most of the previous work published on the subject uses complicated extraction schemes that are expensive and difficult to implement in a commercial or industrial application. Using the method described, the process is optimized by using less costly chaotropic agents, and detergents that are easier to remove, than those previously used. Innovative methods to increase the speed of renaturing the extracted proteins are further provided. Typically, dialysis against water is used to remove the detergent or chaotropic agent. However, by precipitating the proteins with ethanol, ammonium sulfate, or polyethylene glycol, dialysis against water is not necessary. Further, ultrafiltration may be used, thereby avoiding dialysis.

Generally, extracted osteoinductive factors have lower specific bone forming activity when compared to the starting material. This may be caused by protein denaturation that results from the extraction. For example, when guanidine is used to extract the hydrophobic osteoinductive proteins, the proteins lose their native three-dimensional conformation. As a result, unless they regain their normal shape upon removal of the guanidine, they no longer are active. The addition of chemical chaperones to the guanidine solution may prevent this irreversible protein denaturation. Suitable chemical chaperones include glycerol, trehalose, proline, glycine betaine, and dextrose, along with mixtures of these. These chemical chaperones enable the osteoinductive proteins to regain their native three-dimensional conformation when the guanidine is removed. They also prevent protein denaturation during lyophilization.

Thus, a method for extracting osteoinductive factors from the mineral component of bone is provided to recover growth factor activity that is normally lost during the demineralization process. It is known that 4 M guanidine hydrochloride can extract osteoinductive factors from finely powdered mineralized bone. Additionally, osteoinductive factors can be recovered from the acid that is typically used to demineralized bone, such as 0.6 N HCl. These osteoinductive factors are normally lost during the demineralization process and treated as waste.

Growth factors may be extracted from the mineral phase of bone using, for example, the following procedure. As previously described, bone is at least partially demineralized. The bone may comprise powder, fibers, chips, or other. The bone may be demineralized in an acid, for example 1 M citric acid, 2M citric acid, or 0.6N HCl, at temperatures ranging from, for example 1° C. to 28° C. for time period of, for example 10 minutes to 96 hours. In one embodiment, the bone is demineralized in an acid at a temperature of 4° C. After demineralization, the acid used for demineralization contains growth factors and mineral. The acid may be dialyzed against water to cause the mineral phase and the protein growth factors to co-precipitate. This biphasic (protein and mineral) material may then be collected by filtration or centrifutation and combined with a carrier or lyophilized.

In alternative embodiments, the protein and mineral material in the acid may be separated by dialyzing the acid, also referred to as the demineralization bath, against a weak acid, for example 0.25M citric acid. In such embodiment, the mineral phase passes through the dialysis bag and the protein phase (collagen fragments, growth factors, etc.) is left within the bag. The protein phase can then be recovered by dialyzing against water and separating water soluble and water insoluble proteins from one another.

In one embodiment, the method for extracting growth factors comprises demineralizing powdered bone with dilute acid within a dialysis bag. Suitable dilute acid includes 0.05 M to 1.0 M HCl and 1 M or 2M citric acid. After removing the demineralized bone, the contents of the bag may be further dialyzed against dilute acid to remove the mineral components. A volatile acid, such as acetic acid, can be used to facilitate recovery by lyophilization.

Thus, mineralized bone or bone mineral recovered from demineralization acid may be used as a means of purifying recovered proteins. The protein phase recovered from the demineralization bath may be solubilized in urea or other form of detergent solution. The bone stimulating growth factors may then be purified, for example using a hydroxyapatite affinity chromatogrphay scheme, described below.

In one embodiment a protein composition substantially free from inorganic components is provided. The protein composition may comprise less than 5% inorganic components by weight. In an alternative embodiment, a protein composition comprising organic components ranging from approximately 6% to approximately 20% by weight is provided. In another embodiment, a protein composition comprising organic components ranging from approximately 21% to approximately 50% may be provided. In yet a further embodiment, a protein composition comprising organic components ranging from approximately 51% to approximately 90% may be provided. The protein composition may be recovered from acid used to demineralize bone. The proteinaceous material of the protein composition may be purified by chromatography, electrophoresis, or other chemical or physical means. The protein composition may be combined with another material such as demineralized bone, hydroxyapatite, tricalcium phosophate, dicalcium phosphate or other. In some embodiments, the protein composition may exhibit the ability to induce heterotopic bone formation in an athymic animal. In other embodiments the protein composition can serve as a source of collagen Type I and other extracellular matrix proteins that can support tissue repair processes such as angiogenesis, osteoconduction and wound healing. As the protein material has desirable handling properties when combined with water or glycerol, the protein can also serve as a carrier for a variety of bone forming matrices including DBM.

In some embodiments, the protein composition may be solubalized in an appropriate medium, such as 6M urea, exposed to hydroxyapatite, TCP, DCP, mineralized bone, surface demineralized bone, or mineral recovered from acid used to demineralize bone. The protein may further be permitted to adsorb onto the mineral surfaces and be washed with a solution comprising, for example, sodium phosphate ranging from approximately 1 mM to 50 mM in concentration. The proteins may then be eluted with a solution comprising, for example, sodium phosphate ranging in concentrations from between approximately 100 mM to approximately 500 mM.

As is described below, growth factors recovered from the mineral phase of bone may be recombined with an osteoinductive carrier.

Proteases may reduce the activity of the osteoinductive factors in demineralized bone by breaking down those osteoinductive factors. This negative effect may be reduced or eliminated by adding protease inhibitors to the HCl solution. Suitable protease inhibitors for use in the present invention include N-ethyl maleimide, benzamidine HCl, cysteine, or iodoacetic acid. Alternatively, the bone may be heated briefly to inactivate the proteases, which are relatively more heat sensitive than the growth factors. A suitable heating regimen is 5 minutes at 60° C., or 1 minute at 90° C.

In alternative embodiments, extraction of osteoinductive factors from mineralized or demineralized bone may be done in any suitable manner. Further, during extraction, coprecipitates may be used. Thus, for example, bone may be treated with a chaotropic solvent such as guanidine hydrochloride. The bone and chaotropic solvent are dialyzed against water. As the chaotropic solvent decreases, it is replaced by water. Precipitates are then extracted. Coprecipitates, such as protein, collagen, collagen fragments, albumen, or protein with RGD sequences, may be extracted. The extracted osteoinductive factors and coprecipitates may then be blended into a homogenous mixture.

Proteins in bone matrix tend to be insoluble and may associate with the bone matrix. Generally, collagens are among the most insoluble osteoinductive factors. Extraction methods may be used to increase the solubility of the osteoinductive factors to facilitate extraction of the osteoinductive factors. Generally, growth factors are hydrophobic and are not readily soluble. The growth factors may be treated to improve solubility.

The solubility of the demineralized bone in one or more solvents (e.g., an aqueous medium) may be changed, e.g., increased, relative, for example, to the solubility of a standard DBM not exposed to the treatment. Preferably, the aqueous medium is at physiological conditions, e.g., pH, osmotic pressure, salt concentration, etc. are within physiologically appropriate ranges. For example, the pH may be approximately 7.2-8.0, or preferably 7.4-7.6. The osmotic pressure may be approximately 250-350 mosm/kg, 280-300 mosm/kg, etc. More generally, the pH may be between approximately 3-11, 4-10, 5-9, 6-8.5, etc. The osmotic pressure may be between 50-500 mosm/kg, 100-350 mosm/kg, etc. The salt concentration may be approximately 100-300 mM NaCl, e.g., approximately 150 mM NaCl. The aqueous medium may be tissue culture medium, blood, extracellular fluid, etc., and the physiological conditions may be conditions such as are typically found within these fluids and/or within a body tissue such as muscle. The solubility may be increased at any temperature, e.g., room temperature, body temperature of a subject such as a human or animal, etc.

Collagenase treatment of standard human DBM significantly increases its solubility relative to that of untreated standard human DBM. The solubility of the DBM may be increased by exposure to an appropriate treatment or condition, e.g., collagenase treatment, radiation, heat, etc. The extent to which the solubility is increased may be varied by varying the nature of the treatment (e.g., the enzyme concentration) and/or the time over which it is applied. A combination of treatments may be used. In certain embodiments of the invention, the solubility of the human DBM composition is greater than that of a standard DBM composition by between 10% and 4000% percent. For example, the solubility may be greater by between 10% and 100%, 100% and 500%, 500% and 1000%, 1000% and 2000%, 2000% and 3000%, 3000% and 4000% or any other range between 10% and 4000%. The solubility may be assessed at any time following the treatment. For example, the DBM may be placed in aqueous medium for a period of time such as 244-8 hours, 3, 4, 5, 6, or 7 days, 10 days, 14 days, etc. The amount of DBM remaining after the period of time is quantitated (e.g., dry weight is measured) and compared with the amount that was present initially. The extent to which the amount decreases after a period of time serves as an indicator of the extent of solubilization.

Extraction may extract both osteoinductive factors and their inhibitors. If the inhibitors are extracted, it may be desirable in some instances to separate out the osteoinductive factors. This may be referred to as removal of the inhibitors or concentration of the osteoinductive factors.

As a general matter, both the osteoinductive factors and the inhibitors may be extracted and both the osteoinductive factors and the inhibitors may be used for manufacturing the osteogenic osteoimplant. Alternately, only the osteoinductive factors (and not their inhibitors) are extracted and only the osteoinductive factors are used for manufacturing the osteogenic osteoimplant. Lastly, both the osteoinductive factors and the inhibitors may be extracted and only the osteoinductive factors may be used for manufacturing the osteogenic osteoimplant. The embodiment of extraction and resultant use of osteoinductive factors with or without inhibitors is not a limiting feature of the present invention.

In one embodiment, a simplified extraction process is used that is amenable to batch processing. K. Behnam, E. Brochmann, and S. Murray; Alkali-urea extraction of demineralized bone matrix removes noggin, an inhibitor of bone morphogenetic proteins; Connect Tissue Res. 2004, 45(4-5):257-60.

In certain embodiments, the bone is exposed to a treatment or condition that generates peptides and protein fragments having osteoinductive or chondrogenic activity. In contrast to various longer proteins, certain peptides and protein fragments are less susceptible to proteolytic degradation and more likely to maintain their osteoinductive or chondrogenic properties in the proteolytic environment of the matrix or implant site. Many osteoinductive and chondrogenic proteins, for example growth factors such as BMPs, cell signaling molecules, transcription factors, hormones, etc., have domains that are responsible for binding to receptors and/or initiating signal transduction in bone and cartilage growth pathways. These domains are capable of functioning independently as peptides and protein fragments. In certain embodiments, the osteoinductive or chondrogenic activity of bone and cartilage matrices is increased by cleaving the osteoinductive and chondrogenic factors present in the matrix to generate active peptides or protein fragments and/or to generate active peptides or protein fragments that are less susceptible to degradation than their longer precursors. The increased number of factors in the matrix results in increased bone or cartilage formation.

If desired, the osteoinductive factors can be modified in one or more ways, e.g., their protein content can be augmented or modified as described in U.S. Pat. Nos. 4,743,259 and 4,902,296, the contents of which are incorporated by reference herein. As discussed more fully below, the osteoinductive factors can be admixed with one or more optional substances such as binders, fillers, fibers, meshes, substances providing radiopacity, plasticizers, biostatic/biocidal agents, surface active agents, and the like, prior to, during, or after adding to the carrier.

A number of naturally occurring proteins from bone or recombinant osteoinductive factors have been described in the literature and are suitable for use in the osteoinductive composition. Recombinantly produced osteoinductive factors have been produced by several entities. Creative Biomolecules of Hopkinton, Mass., produces an osteoinductive factor referred to as Osteogenic Protein 1, or OP1. Genetics Institute of Cambridge, Mass., produces a series of osteoinductive factors referred to as Bone Morphogenetic Proteins 1-13 (i.e., BMP 1-13), some of which are described in U.S. Pat. Nos. 5,106,748 and 5,658,882 and in PCT Publication No. WO 96/39,170, each herein incorporated by reference. Purified osteoinductive factors have been developed by several entities. Collagen Corporation of Palo Alto, Calif., developed a purified protein mixture that is purported to have osteogenic activity, as described in U.S. Pat. Nos. 4,774,228, 4,774,322, 4,810,691, and 4,843,063, each herein incorporated by reference. Urist developed a purified protein mixture which is purported to be osteogenic, as described in U.S. Pat. Nos. 4,455,256, 4,619,989, 4,761,471, 4,789,732, and 4,795,804, each herein incorporated by reference. International Genetic Engineering, Inc. of Santa Monica, Calif., developed a purified protein mixture that is purported to be osteogenic, as described in U.S. Pat. No. 4,804,744, herein incorporated by reference.

One osteoinductive factor that may be used in the osteoinductive composition is described in detail in U.S. Pat. No. 5,290,763, herein incorporated by reference. This osteoinductive factor has a high osteogenic activity and degree of purity. The osteoinductive factor of the '763 patent exhibits osteoinductive activity at about 3 micrograms when deposited onto a suitable carrier and implanted subcutaneously into a rat. In one embodiment, the osteoinductive factor is an osteoinductively active mixture of proteins that exhibit the gel separation profile shown in FIG. 1 of U.S. Pat. No. 5,563,124, herein incorporated by reference.

In some embodiments, bone stimulating growth factors, for example recovered from the mineral phase of bone, may be purified using a apatite affinity chromatography scheme. Thus, mineralized or surface demineralized bone may be used as a chromatography resin. Bone mineral comprises calcium phosphate sales similar to hydroxyapatite. To use mineralized or surface demineralized bone as a chromatography resin, excess lipid and protein may be removed from the surfaces of the bone. In other embodiments, a similar scheme may be done using demineralized bone matrix as a resin. In yet further embodiments, recovered inorganic bone mineral (sintered or unsintered) may be used as the chromatography resin.

In one embodiment, the protocol for such scheme may be as follows. Mineralized bone particles, for example ranging from 100 μm to 5 mm, are prepared. The surface of the mineralized bone particles is cleaned, for example by soaking or stirring the bone particles in a dilute base such as 0.1 M NaOH for several minutes. Generally, such surface cleaning removes proteins as well as lipids. In alternative embodiments, surface cleaning may be performed using supercritical $CO_2$. Growth factor extracts from the mineral phase may be solubalized in a chaotropic solvent such as 6M urea. The growth factor solution may then be mixed with the mineralized bone particles, for example, for several minutes. During such mixing, proteins having an affinity for hydroxyapatite bind to the bone surfaces. The bone-protein complex is then precipitated and the supernatant removed. The bone-protein complex may be treated to remove weakly bound proteins such as collagen fragments while retaining osteoinductive proteins (the osteoinductive proteins remain bound to the material). Such treatment may comprise treating the bone-protein complex with a 6M urea containing low concentrations of sodium phosphate. The treated bone-protein complex may be centrifuged and the supernatant aspirated. In some embodiments, the bone-protein complex may be treated with urea containing higher concentrations of sodium phosphate (e.g., 100 mM, 180 mM, or 250 mM) to release bound osteoinductive proteins. Alternatively, the bone-osteoinductive protein complex may be lyophilized and formulated with a carrier, for example for orthopedic applications. Further, the bone protein comples may be used as a growth factor microcarrier that can be distributed in a DBM macrocarrier.

In yet a further embodiment, an osteoinductive composition with reduced immunogenicity is provided. The osteoinductive composition comprises noncollagenous proteins and mineral recovered acid. The noncollagenous proteins may be extracted from demineralized bone or recovered from acid used to demineralize bone. The mineral recovered acid may be from acid used to demineralize bone. The noncallegnous proteins and mineral recovered acid may be combined such that the osteoinductive composition exhibits the ability to induce the formation of heterotopic bone in a normal (euthymic) mouse.

V. Optional Processing

As mentioned above, in some instances it may be desirable to remove inhibitors or concentrate the osteoinductive factors. This is optional and may be done by any suitable method. Generally, it may be desirable to remove the inhibitors quickly without denaturing the osteoinductive factors.

Suitable osteoinductive factors may be obtained by purification of naturally occurring proteins from bone or by recombinant DNA techniques. As used herein, the term recombinantly produced osteoinductive factors refers to the production of osteoinductive factors using recombinant DNA technology. For example, nucleic acids encoding proteins having osteogenic activity can be identified by producing antibodies that bind to the proteins. The antibodies can be used to isolate, by affinity chromatography, purified populations of a particular osteogenic protein. The amino acid sequence can be identified by sequencing the purified protein. It is possible to synthesize DNA oligonucleotides from the known amino acid sequence. The oligonucleotides can be used to screen either a genomic DNA and/or cDNA library made from, for example, bovine DNA, to identify nucleic acids encoding the osteogenic protein. The correct oligo-nucleotide will hybridize to the appropriate cDNA, thereby identifying the cDNA encoding the osteogenic protein encoding gene.

In other embodiments, the DBM may include and/or be treated with agents that inhibit the activity of one or more activating enzymes, proteases, or glycosidases. Such inhibitory agents are expected to reduce the activity of specific enzymes (whether derived from the host or from the DBM) that would otherwise interact with osteoinductive agents or other active agents in the DBM, thereby reducing osteoinductivity or wound healing.

The treatment or condition may cleave an inhibitory factor that would otherwise inhibit a positively acting agent (by which is meant an agent that enhances a biological activity of the bone matrix). For example, a variety of proteins or protein fragments are known to inhibit the osteoinductive and/or osteogenic activity of certain bone morphogenetic proteins such as BMP-2. In certain embodiments the inhibitory effect of a protein or protein fragment is reduced by exposing to a treatment or condition that causes the cleavage or degradation of the inhibitory agent. The treatment or condition may block the interaction of the inhibitory agent with its target (e.g., BMP-2) or may inhibit synthesis, secretion, post-translational modification, transport, etc., of the inhibitory agent. For example, the bone may be exposed to antibody to an inhibitory agents or the antibody can be added to the bone.

As will be appreciated by those skilled in the art, factors having osteoinductive, osteogenic, and/or chondrogenic activity can be inhibited by a variety of mechanisms including proteolytic degradation, binding or sequestration of the factor, etc. A variety of proteins or protein fragments inhibit the osteoinductive and/or osteogenic activity of certain bone morphogenetic proteins, such as BMPs-2, -4, -5, -6, and -7. Among these inhibitory agents are noggin, chordin, gremlin, Dan, Cerberus, the protein related to Dan and Cerberus (PRDC), caronte, Dante, sclerostin, follistatin, follistatin-related gene (FLRG), ventroptin, and alpha2 HSglycoprotein. Noggin blocks the effect of BMPs in cells of the osteoblastic lineage, and the addition of noggin to osteoblasts in culture blocks BMP-induced synthesis of collagen and noncollagen proteins, and also inhibits the stimulatory effect of BMPs on alkaline phosphatase activity. Chordin acts in a similar fashion. Further details regarding these inhibitory agents are found in Canalis, supra, and references cited therein.

Certain collagen fragments are also believed to inhibit BMPs. For example, a potentially inhibitory collagen fragment corresponds to the C-terminal end of procollagen that is released during extracellular matrix remodeling and collagen assembly. The sequence for a chordin-like collagen fragment (from Type I collagen) is YVEFQEAGSC VQDGQRYNDK DVWKPEPCRI CVCDTGTVLC DDIICEDVKD CLSPEIPFGECCPICPADLAAAA (SEQ ID NO: 1).

Bone or cartilage inhibitory factors (BCWF) can be inactivated or inhibited by a variety of methods. For example, a specific protease that cleaves or degrades the BCIF can be used. Another approach is to use an antibody that binds to the BCIF and blocks its interaction with a positively acting factor such as BMP-2 or BMP-4. The antibody may inhibit post-translational modification, transport, etc., of the inhibitory agent. Antibodies to the inhibitory agents mentioned herein (and others) are known in the art or could be generated using known methods without undue experimentation. Either polyclonal or monoclonal antibodies, or antigen-binding fragments thereof, can be used. Other agents having specific binding ability (e.g., affibodies) could likewise be used. One of ordinary skill in the art will be able to generate appropriate antibodies, affibodies, etc., based upon the known sequences of the inhibitory proteins.

VI. Provide a Carrier

Thus, the extracted osteoinductive factors (and possibly inhibitors) may be added to a carrier. For ease of reference, unless otherwise noted, reference to osteoinductive factors refers to osteoinductive factors with or without inhibitors. When the osteoinductive factors are added to a carrier, the carrier acts first as a bulking means for applying a small amount of extracted material. The carrier also may serve as a scaffold, and may aid in controlling release kinetics. Suitable carriers include DBM, including surface demineralized bone; mineralized bone; nondemineralized cancellous scaffolds; demineralized cancellous scaffolds; particulate, demineralized, guanidine extracted, species-specific (allogenic) bone; specially treated particulate, protein extracted, demineralized, xenogenic bone; collagen; synthetic hydroxyapatites; polymers; hydrogels; starches; polyethylene glycol, tricalcium phosphate, sintered hydroxyapatite, settable hydroxyapatite; polylactic acid; tyrosine polycarbonate; calcium sulfate; collagen sheets; settable calcium phosphate; polymeric cements; settable poly vinyl alcohols, polyurethanes; resorbable polymers; polysaccharides and other large polymers; liquid settable polymers; and other biocompatible settable materials. Settable materials may be used, and they may set up either in situ, or prior to implantation. Optionally, xenogenic bone powder carriers also may be treated with proteases such as trypsin. Preferably, xenogenic carriers are treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The osteoinductive factors and carrier (or delivery or support system) together form an osteoimplant useful in clinical applications.

Any suitable shape, size, and porosity of carrier may be used. Rat studies show that the new bone is formed essentially having the dimensions of the device implanted. Generally, particle size influences the quantitative response of new bone; particles between 70 µm and 420 µm elicit the maximum response. However, other particle sizes may be used. Contamination of the carrier with bone mineral may inhibit bone formation.

In some embodiments, the carrier may be settable and/or injectable. Such carrier may be, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, which are hereby incorporated by reference.

A successful carrier for osteoinductive factors performs several functions. It carries osteoinductive factors and allows appropriate release kinetics. A successful carrier also appropriately accommodates each step of the cellular response during bone development, and in some cases protects the osteoinductive factors from nonspecific proteolysis. In addition, selected materials must be biocompatible in vivo and optionally biodegradable. In some uses, the carrier must act as a temporary scaffold until replaced completely by new bone. Polylactic acid (PLA), polyglycolic acid (PGA), and various combinations have different dissolution rates in vivo. In bone, the dissolution rates can vary according to whether the implant is placed in cortical or trabecular bone.

The carrier may comprise a shape-retaining solid made of loosely adhered particulate material, e.g., with collagen. It may also comprise a molded, porous solid, or simply an aggregation of close-packed particles held in place by surrounding tissue. Masticated muscle or other tissue may also be used. Large allogenic bone implants may act as a carrier if their marrow cavities are cleaned and packed with particles and the osteoinductive factors.

The osteoimplant resulting from the carrier and the osteoinductive factors may assume a determined or regular form or configuration such as a sheet, plate, disk, tunnel, cone, or tube, to name but a few. Prefabricated geometry would include, but not be limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision.

In one embodiment, the osteoimplant induces endochondral bone formation reliably and reproducibly in a mammalian body. The carrier comprises particles of porous materials. The pores must be of a dimension to permit progenitor cell migration into the carrier and subsequent differentiation and proliferation. The particle size should be within the range of 70 .mu.m-850 µm, preferably 70 µm-420 µm, most preferably 150 µm-420 µm. It may be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation. Useful carrier materials include collagen; homopolymers or copolymers of glycolic acid, lactic acid, and butyric acid, including derivatives thereof; and ceramics, such as hydroxyapatite, tricalcium phosphate and other calcium phosphates. Combinations of these carrier materials also may be used.

Mineralized or surface demineralized bone particles may alternatively be used as a carrier. Thus, an osteoinductive composition comprising mineralized or surface demineralized bone particles and extracts of DBM is provided. The DBM extracts may be adsorbed to the surfaces of the mineralized or partially demineralized bone particles. Weakly bound components may be eluted using, for example, low concentrations of sodium phosphate (for example, 5 mM to 50 mM), thereby concentrating the growth factors. In some embodiments, analysis of the proteins bound to the surfaces of the mineralized or surface demineralized bone particles indicaes a ratio of Histone H2A to total protein bound elevated by a factor of 2 to 10,000 times over the normal ratio found in extracts of demineralized bone matrix or protein recovered from acid used to demineralize bone. In some embodiments, analysis of the proteins bound to the surfaces of the mineralized or surface demineralized bone particles indicates a ratio of Secreted Phosphoprotein 24 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the mineralized or surface demineralized bone particles indicates a ratio of BMP-2 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the mineralized or surface demineralized bone particles indicates a ratio of BMP-4 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the mineralized or surface demineralized bone particles indicates a ratio of TGF-Beta to total protein bound elevated by a factor of 2 to 10,000 times over the normal ratio found in extracts of demineralized bone matrix or protein recovered from acid used to demineralize bone.

Use of DBM as Carrier

Any of a variety of DBM preparations may be used as a carrier. DBM prepared by any method may be employed, including particulate or fiber-based preparations, mixtures of fiber and particulate preparations, fully or partially demineralized preparations, mixtures of fully and partially demineralized preparations, and surface demineralized preparations. See U.S. Pat. No. 6,326,018, Reddi et al, *Proc. Natl. Acad. Sci. USA* (1972) 69:1601-1605; Lewandrowski et al., *Clin. Ortho. Rel. Res.*, (1995) 317:254-262; Lewandrowski et al., *J. Biomed. Mater. Res.* (1996) 31:365-372; Lewandrowski et al. *Calcified Tiss. Int.*, (1997) 61:294-297; Lewandrowski et al., *I Ortho. Res.* (1997) 15:748-756, each of which is incorporated herein by reference. Preferred demineralized bone matrix compositions are described in U.S. Pat. No. 5,507,813, herein incorporated by reference. The DBM may be in the form of a section that substantially retains the shape of the original bone (or a portion thereof) from which it was derived. Also useful are DBM preparations comprising additives or carriers such as polyhydroxy compounds, polysaccharides, glycosaminoglycan proteins, nucleic acids, polymers, polaxomers, resins, clays, calcium salts, and/or derivatives thereof.

The DBM component may be ground or otherwise processed into particles of an appropriate size before or after demineralization. In certain embodiments, the particle size is greater than 75 microns, more preferably ranging from about 100 to about 3000 microns, and most preferably from about 200 to about 2000 microns. After grinding the DBM component, the mixture may be sieved to select those particles of a desired size. In certain embodiments, the DBM particles may be sieved though a 50 micron sieve, more preferably a 75 micron sieve, and most preferably a 100 micron sieve.

One way to protect small size particles from cellular ingestion and/or provide a diffusion barrier is to embed them in a monolithic bioabsorbable matrix, and then fragment the particle-containing monolithic matrix into particle sizes greater than 70 microns, preferably greater than 100 microns, and most preferably greater than 150 microns in their smallest dimension. Preferred matrices for embedding small DBM particles include biocompatible polymers and setting calcium phosphate cements. Generally the particulate DBM/polymer weight ratio will range from about 1:5 to about 1:3. In the case of calcium phosphate, the DBM will be present up to 75% by weight. Particulation of the monolith can be accomplished by conventional milling or grinding, or through the use of cryomilling, or freezing followed by pulverization. In one embodiment, lyophilized DBM is embedded in a resorbable polymer. In a further embodiment, lyophilized DBM is embedded in one of the setting calcium phosphates known to the art.

Following particulation, the DBM is treated to remove mineral from the bone. While hydrochloric acid is the industry-recognized demineralization agent of choice, the literature contains numerous reports of methods for preparing DBM (see, for example, Russell et al., *Orthopaedics* 22(5): 524-531, May 1999; incorporated herein by reference). Any material that provides a scaffolding containing active osteoinductive factors is considered DBM. The DBM may be prepared by methods known in the art or by other methods that can be developed by those of ordinary skill in the art without undue experimentation. In some instances, large fragments or even whole bone may be demineralized, and then particulated following demineralization.

In one embodiment, an osteoinductive composition comprising partially demineralized bone matrix particles is provided. The partially demineralized bone matrix particles may, for example, range in size from 500 μm to 4 mm. In one embodiment 10-80% of the mineral of the mineral content of the bone is removed. The partially demineralized bone may be heated to temperatures ranging from approximately 40° C. to approximately 120° C. for period of time ranging from approximately 1 minute to approximately 96 hours. Heating may be done with the partially demineralized bone in a dry state, in distilled water, in a neutral buffer solution, or other. The osteoinductive composition may exhibit the ability to induce the formation of heterotopic bone in a higher order animal such as a dog, human, or sheep. In some embodiments, the osteoinductive composition may be combined with osteoinductive growth factors extracted from bone, recovered from acid used to demineralized bone, or other.

Mixtures of one or more types of demineralized bone-derived elements can be employed. Moreover, one or more of types of demineralized bone-derived elements can be employed in combination with non-demineralized bone-derived elements, i.e., bone-derived elements that have not been subjected to a demineralization process. Thus, e.g., the weight ratio of non-demineralized to demineralized bone elements can broadly range from about 0:1 to about 1:0. Suitable amounts can be readily determined by those skilled in the art on a case-by-case basis by routine experimentation.

An osteoinductive demineralized bone matrix scaffold is thus further provided. In one embodiment, the osteoinductive demineralized bone matrix scaffold comprises bone derived components and exhibits, without collagenase pretreatement, the ability to induce specific alkaline phosphotase activity levels higher than those of standard demineralized bone matrix preparations, for example, 2 to 100,000,000 higher than standard demineralized bone matrix preparations in cultured C2C12 cells. In another embodiment, the osteoinductive demineralized bone matrix scaffold comprises osteoinductive growth factors, for example extracted from DBM or recovered from acid baths used for demineralization of the bone matrix, and demineralized bone matrix and exhibits the ability to induce specific alkaline phosphotase activity levels higher than those of standard demineralized bone matrix preparations, for example, 2 to 100,000,000 higher than standard demineralized bone matrix preparations in cultured C2C12 cells.

In addition to the demineralizing step, the bone is optionally subjected to a configuring step to form an implant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles are disclosed in U.S. Pat. Nos. 5,507,813 and 6,436,138, respectively, the contents of which are incorporated by reference herein. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," *Biomaterials*, 24(15):2593-603, 2003. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

The bone used in creating the bone matrix may be obtained from any source of living or dead tissue. Often, it will be preferred that the source of bone be matched to the eventual recipient of the inventive composition. At a minimum, it is often desirable that the donor and recipient are of the same species, though even xenogenic sources are permitted. Thus for use in humans, it is generally preferred to use DBM derived at least in part from human bone. For example, the bone material may be at least 10%, 20%, 30%, 40%, 50%, 60%, 70%, 80%, 90% or more human bone material. In certain embodiments 100% of the bone material is human bone material.

The matrix may be completely insoluble or may be slowly solubilized after implantation. Following implantation, preferred matrices resorb or degrade, remaining substantially intact for at least one to seven days, most preferably for two or four weeks or longer and often longer than 60 days. Bioactive agents may be endogenously present in the matrix as in the case of most demineralized bone, or they may be exogenously added to the matrix. Matrices may also comprise combinations of endogenous and exogenous bioactive agents.

The matrix may comprise a number of materials in combination, some or all of which may be in the form of fibers and/or particles. The matrix may comprise calcium phosphates. Driessens et al. "Calcium phosphate bone cements," Wise, D. L., Ed., *Encyclopedic Handbook of Biomaterials and Bioengineering*, Part B, Applications New York: Marcel Decker; Elliott, *Structure and Chemistry of the Apatites and Other Calcium Phosphates* Elsevier, Amsterdam, 1994, each of which is incorporated by reference. Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites.

In one embodiment, an osteoinductive material is provided comprising a mineralized particulated material, osteoinductive growth factors, and a demineralized bone matrix scaffold. The mineralized particulated material may be TCP, hydroxyapatite, mineral recovered from bone, cancellous chips, cortical chips, surface demineralized bone, or other material. The osteoinductive growth factors may be synthetically derived, extracted from demineralized bone matrix, recovered from demineralization acid bath, or other. The demineralized bone matrix scaffold may be combined with a carrier such as starch or glycerol. In various embodiments, the osteoinductive growth factors may be solubilized and combined with the mineralized particulate material, thus allowing adsorption of the growth factors onto the mineral surfaces, as previously described. The growth factor/mineral composite may then be distributed throughout the demineralized bone matrix scaffold. The growth factor/mineral composite thus may comprise a microcarrier and the demineralized bone matrix scaffold may comprise a macrocarrier. The size of the microcarrier mineralized particles may range, for example, from 50 nm to 5 mm.

In another embodiment, an osteoinductive composition with reduced immunogenicity is provided comprising noncollagenous proteins and a demineralized bone matrix scaffold. The noncaollagenous proteins may be extracted, for example, from demineralized bone or recovered from acid used to demineralize bone. The noncollagenous proteins and the demineralized bone matrix scaffold may be combined such that the osteoinductive composition exhibits the ability to induce the formation of heterotopic bone in a normal (euthymic) mouse.

Treatment of Carrier

In other embodiments, the present invention further provides methods of increasing the osteoinductivity of a carrier by exposing the carrier to at least one treatment (e.g., a biological or chemical agent). In addition to dispersion of the extracted osteoinductive factors onto the carrier, the carrier may be exposed to a chemical or condition that selectively degrades inhibitors of osteogenic activity and/or to a chemical or condition that activates osteoinductive factors in the carrier. Thus, the resulting carrier has an increased osteoinductivity, osteogenic, or chondrogenic activity compared to a similar carrier not exposed to the treatment or condition, because inhibition of an osteoinductive, osteogenic, or chondrogenic factor is blocked. In general, agents that inhibit or reduce osteoinductive, osteogenic, or chondrogenic activity may be referred to as bone/cartilage inhibitory factors (BCIF).

Reduction of Inhibitors

As stated above, the carrier may be treated to reduce inhibitors of osteoinductive factors. As will be discussed more fully below, the extracted osteoinductive factors are added to the carrier. The addition of the osteoinductive factors and the treatment of the carrier to reduce inhibitors may be performed in combination or sequentially. One or more rounds of treatment may be used, i.e., the treatments may alternate.

Thus, the carrier may be treated to cleave or degrade a specific protein such as an inhibitor of BMP. The carrier is treated such that a specific protein that is not a major structural component of the carrier is affected. The specific protein generally makes up less than 1% of the dry weight of the matrix, e.g., less than 0.5%, less than 0.1%, etc. The specific protein can be a negatively acting factor, e.g., an inhibitor of a BMP or an inhibitor of a BMP signaling pathway, wherein cleavage or degradation of the inhibitor allows increased activity of the protein that it would otherwise inhibit.

Alternatively or additionally, the carrier may include inhibitory agents presented in a time-release formulation (e.g., encapsulated in a biodegradable polymer). In the case of activating enzymes, i.e., enzymes that lead to the release, presentation, or creation of osteoinductive factors), inhibitory agents that reduce the activity of activating enzymes preferably lead to increased osteoinductivity over an extended period of time rather than just a burst just after implantation.

Activation

Certain of the osteoinductive or chondrogenic factors found in a bone or cartilage matrix are in cryptic form and must be "activated" or "released" to be osteoinductive. The activation of osteoinductive factors may involve a conformational change, a post-translational modification, protein cleavage, a change in tertiary or quaternary structure, or release from a binding protein. The osteoinductive factors, either those extracted and added to the carrier or those already present in the carrier, may be in a pre- or pro-form, which requires proteolytic cleavage to be active. The osteoinductive factors also may be associated with a binding protein or a protein of a bone or cartilage matrix. Proteolysis may also be involved in the activation or inactivation of a binding protein, which could result in activation of the osteoinductive peptide or protein fragment. Therefore, all treatments of a bone or cartilage matrix with any specific or non-specific condition may affect activation rates of osteoinductive peptides and protein fragments.

The presence or activation of peptides and/or protein fragments having osteoinductive or chondrogenic activity may compensate for degradation of osteoinductive or chondrogenic proteins in the carrier, which may occur during preparation of the carrier. In certain embodiments it may be desirable to both inhibit the degradation of osteoinductive or chondrogenic factor and activate or add osteoinductive or chondrogenic factors such as osteoinductive or chondrogenic peptides or protein fragments. Variables such as pH and ion concentration may affect protein function and/or folding of the peptide or protein fragment, and may affect the activation of osteoinductive or chondrogenic factors. These variables also may affect the release of an osteoinductive factor from its binding protein. For example, where pH plays a role in the activation of a factor, the carrier may include a chemical compound such as a polymer that will break down over time and release an acid by-product; thereby activating the osteoinductive factors within the carrier. Alternatively, a biodegradable polymer may release ions or a protease that is able to "activate" the osteoinductive factors of the carrier.

In certain embodiments, one or more enzymes, such as proteases, lipases, and glycosidases, are added to the carrier to activate the osteoinductive or chondrogenic factors already present (e.g., to convert one or more osteoinductive factors from an inactive to an active form or from an active form to a more active form, or from a form that is susceptible to degradation to a form that is less susceptible to degradation, e.g., a form that has a longer half-life).

Many of the growth factors responsible for the osteoinductive or chondrogenic activity of a carrier, such as a bone matrix carrier, exist in cryptic form, in the carrier, until activated. Activation can involve the change of a pre or pro function of a factor, or release of the function from a second factor or entity, which binds to the first growth factor. For example, proteolytic cleavage results in separation of the inactive proprotein (e.g., a proprotein from the TGF superfamily of proproteins, e.g., TGF-(3) and release of an active, mature peptide). As proteins of bone and cartilage matrices degrade naturally or artificially, they break down into peptides and protein fragments that contain active domains and function as receptor ligands and signal transducers in bone and cartilage growth signaling pathways. These reactions may be promoted to enhance osteoinductive and chondrogenic signaling in the carrier.

Generate Osteoinductive Peptides and/or Protein Factors in the Carrier

A wide variety of agents, selected from biological agents such as enzymes, chemicals, and conditions, can be used to generate osteoinductive peptides and protein fragments, and these are well known in the art. The proteases, chemicals, and conditions of the present invention can be site specific, amino acid site specific, protein specific, semi-site-specific, lipid specific, or sugar specific. Enzymes may be obtained from endogenous, exogenous, autogenic (autologous), allogenic, or xenogenic sources. They may be purified from natural sources or produced recombinantly. In many embodiments the enzymes are purchased from commercial sources (Worthington Biochemical Industries, Sigma, etc.) and either used directly or subsequently purified to be free of contaminants that may negatively affect the activity of the final product. Enzymes, peptides, or protein fragments (e.g., generated by particular proteases) and other treatments may also be purified by conventional methods. Sambrook et al., Molecular Cloning: A Laboratory Manual, Cold Spring Harbor Press, N.Y.; Ausubel et al. "Current Protocols in Molecular Biology, Greene Publishing Associates, New York, V 1 & 2 1996. Purification can be carried out by a variety of chromatographic techniques. Size exclusion chromatography is commonly used. Other methods include ion exchange, hydrophobic interaction, and affinity chromatography. Peptides or protein fragments may be used in the bone or cartilage repair matrix as unpurified preparations as long as the peptides or protein fragments maintain their osteoinductive or chondrogenic activity. Alternatively, the enzymes, peptides, or protein fragments can be synthesized artificially using conventional techniques, produced recombinantly, etc. It may be preferable to use preparations having a high degree of purity. For example, an enzyme preparation may contain at least 90%, at least 95%, at least 98%, at least 99% of the enzyme by weight. The preparation may be essentially free of bacterial components, particularly bacterial components that could cause inflammatory or immunological reactions in a host, such as endotoxin, lipopolysaccharide, etc. Preparations having a purity greater than 99.5% can be used.

One suitable protease is a collagenase. Collagenases and their activity on collagens of various types have been extensively studied. A number of collagenase preparations are available from Worthington Biochemical Corporation, Lakewood, N.J. As described on the company's web site and known in the art, collagen consists of fibrils composed of laterally aggregated, polarized tropocollagen molecules (MW 300,000). Each tropocollagen unit consists of three helically wound polypeptide a-chains around a single axis. The strands have repetitive glycine residues at every third position and numerous proline and hydroxyproline residues, with the particular amino acid sequence being characteristic of the tissue of origin. Tropocollagen units combine uniformly to create an axially repeating periodicity. Cross linkages continue to develop and collagen becomes progressively more insoluble and resistant to lysis on aging. Gelatin results when soluble tropocollagen is denatured, for example on mild heating, and the polypeptide chains become randomly dispersed. In this state the strands may readily be cleaved by a wide variety of proteases.

In general, a variety of different collagenases known in the art can be used. Collagenases are classified in section 3.4.24 under the International Union of Biochemistry and Molecular Biology (NC-IUBMB) enzyme nomenclature recommendations (see, e.g., 3.4.24.3, 3.4.24.7, 3, 4.24.19). The collagenase can be of eukaryotic (e.g., mammalian) or prokaryotic (bacterial) origin. Bacterial enzymes differ from mammalian collagenases in that they attack many sites along the helix. Collagenase may cleave simultaneously across all three chains or attack a single strand. Preferably the collagenase cleaves Type I collagen, e.g., degrades the helical regions in native collagen, preferentially at the Y-Gly bond in the sequence Pro-Y-Gly-Pro-, where Y is most frequently a neutral amino acid. This cleavage yields products susceptible to further peptidase digestion. Any protease having one or more of these activities associated with collagenase may be used as a collagenase in accordance with the present invention.

It will be appreciated that crude collagenase preparations contain not only several collagenases, but also a sulfhydryl protease, clostripain, a trypsin-like enzyme, and an aminopeptidase. This combination of collagenolytic and proteolytic activities is effective at breaking down intercellular matrices, the essential part of tissue disassociation. Crude collagenase is inhibited by metal chelating agents such as cysteine, EDTA, or o-phenanthroline, but not DFP. It is also inhibited by α2-macroglobulin, a large plasma glycoprotein. $Ca^{2+}$ is required for enzyme activity. Therefore, it may be desirable to avoid collagenase inhibiting agents when treating bone matrix with collagenase. In addition, although the additional proteases present in some collagenase preparations may aid in breaking down tissue, they may also cause degradation of desired matrix constituents such as growth factors. Therefore, it may be desirable to use a highly purified collagenase that contains minimal secondary proteolytic activities along with high collagenase activity. For example, a collagenase preparation may contain at least 90%, at least 95%, at least 98%, at least 99% collagenase by weight. The preparation may be essentially free of bacterial components, particularly bacterial components that could cause inflammatory or immunological reactions in a host, such as endotoxin, lipopolysaccharide, etc. Preparations having a purity greater than 99.5% can be used. A suitable preparation is chromatographically purified CLSPA collagenase from Worthington Biochemical Corporation. It may be desirable to include various protease inhibitors that do not inhibit collagenase but that inhibit various proteases that digest BMP. For example, protease inhibitors that are known to protect BMP activity from degradation include N-ethyl maleimide, benzamidine hydrochloride, iodoacetic acid, PMSF, AEBSF, E-64. Bestatin may also be used, particularly if the preparation contains aminopeptidase activity. Any of these protease inhibitors (or others) can be included in a carrier, such as a bone matrix composition, or in any composition that is used to treat a carrier.

Another suitable protease bone morphogenetic protein I (BMP-1). BMP-1 is a collagenolytic protein that has also been shown to cleave chordin (an inhibitor of BMP-2 and BMP-4). Thus, BMP-I may be of use to alter the physical structure of the carrier (e.g., by breaking down collagen) and/or to cleave specific inhibitory protein(s), e.g., chordin or noggin. Proteins related to any of the proteases described herein, i.e., proteins or protein fragments having the same cleavage specificity, can also be used. It will be appreciated that variants having substantial sequence identity to naturally occurring protease can be used. For example, variants at least 80% identical over at least 50%, at least 60%, at least 70%, at least 80%, at least 90%, or 100% of the length of naturally occurring protease (or any known active fragment thereof that retains cleavage specificity) when aligned for maximum identity allowing gaps can be used.

Certain preferred proteases include members of the proprotein convertase (PPC) family of proteases, such as furin and related proteases. Members of this family of cellular enzymes cleave most prohormones and neuropeptide precursors. Numerous other cellular proteins, some viral proteins, and bacterial toxins that are transported by the constitutive secretory pathway are also targeted for maturation by PCs. Furin and other PC family members share structural similarities that include a heterogeneous ~10 kDa amino-terminal proregion, a highly conserved ~55 kDa subtilisin-like catalytic domain, and carboxyl-terminal domain that is heterogeneous in length and sequence. These enzymes become catalytically active following proregion cleavage within the appropriate cellular compartment. Furin is the major processing enzyme of the secretory pathway and is localized in the trans-golgi network. van den Ouweland, A. M. W. et al. (1990) Nucl. Acid Res. 18, 664; Steiner, D. F. (1998) Curr. Opin. Chem. Biol. 2, 31-39. Substrates of furin include blood clotting factors, serum proteins, and growth factor receptors such as the insulin-like growth factor receptor. Bravo D. A. et al. (1994) J. Biol. Chem. 269, 25830-25873. The minimal cleavage site for furin is Arg-X-X-Arg. However, the enzyme prefers the site Arg-X-(Lys/Arg)-Arg. An additional arginine at the P6 position appears to enhance cleavage. Krysan D. J. et al. (1999) J. Biol. Chem. 274, 2322923234. Furin is inhibited by EGTA, α1-antitrypsin Portland, Jean, F. et al. (1998) Proc. Natl. Acad. Sci. USA 95, 7293-7298, and polyarginine compounds, Cameron, A. et al. (2000) J. Biol. Chem. 275, 36741-36749. Furin has been shown to proteolytically process both proTGF and proBMP proteins, for example, pro-TGF-β and proBMP-4, respectively, resulting in the release of the active mature form for each molecule. Dubois et al., American Journal of Pathology (2001) 158(1):305-316; Cui et al., The Embo Journal (1998) 17(16):47354743; Cui et al., Genes & Development (2001) 15:2797-2802, each incorporated by reference herein. Furin has also been shown to cleave BMP-2, BMP-6, and BMP-7. For example, furin cleaves between amino acids 282 and 283 in mature human BMP-2. Newly synthesized human BMP-2 contains a signal sequence (amino acids 1-23), a propeptide (amino acids 24-282), and an active portion (amino acids 283-396). Furin cleaves mature BMP-2 (amino acids 24-396) between amino acids 282 and 283 to release the propeptide and the active molecule.

Thus, the carrier, such as a DBM matrix, may be treated with PPCs such as furin and/or other proteases, which process immature TGF-β and/or BMP superfamily propeptides into their active mature forms and/or process active or inactive TGF-β and/or BMP superfamily polypeptides into smaller active fragments that are resistant to degradation or inactivation relative to the longer polypeptide, generates a carrier with increased osteoinductivity compared to a carrier lacking the protease, resulting in improved bone formation. The higher titers of the mature and/or degradation resistant species in these preparations increase the osteoinductive capacity of the carrier.

Allogenic cancellous demineralized bone is known not to be osteoinductive. When treated with collagenase enzymes for periods routinely used in the art, such as 24 hours, allogenic cancellous demineralized bone remains nonosteoinductive. Applicants have made the surprising discovery that allogenic cancellous bone, when treated with collagenase enzymes for approximately one hour, becomes osteoinductive, approximately as osteoinductive as allogenic cortical demineralized bone. While not desiring to be bound by any particular scientific theory, applicants state that it is believed that the disruption of the collagen matrix makes osteoinductive factors bioavailable. Many types of collagenalytic enzymes, such as those set forth herein, would be expected to render allogenic cancellous demineralized bone osteoinductive when treated as described herein. Other treatments also are expected to provide the same result, including the use of salts or ionizing or electromagnetic radiation, or various categories of enzymes, so long as the enzymes disrupt the collagen without damaging the osteoinductive factors.

Delivery System

The carrier and the method of adding osteoinductive factors to the carrier, discussed more fully below, may result in an enhanced delivery system. More specifically, the osteoinductive factors may be added to a carrier such that the osteoinductive factors are generally evenly dispersed in three dimensions as opposed to superficially coating a carrier. Dispersion throughout the carrier affects control of release kinetics of the osteoinductive factors from the carrier. In one embodiment, a plurality of thin sheets of carrier are provided. Each sheet of carrier is layered with osteoinductive factors. These sheets of carrier layered with osteoinductive factors are stacked.

Thus, optionally, the osteoimplant is formed as a laminate. A laminate osteoimplant may advantageously be shaped in three dimensions, as in the introduction of a concave surface shape. Further, each layer of the laminate is continuous, without requiring binding of the joints between the pieces.

Assembling the superimposed layers into a strong unitary structure may be accomplished by a variety of means/procedures, e.g., application of known and conventional biologically compatible adhesives such as the cyanoacrylates; epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, etc., and protein-based binders such as fibrin glues and mussel-derived adhesive proteins; the use of mechanical fasteners such as pins, screws, dowels, etc., which can be fabricated from natural or synthetic materials and bioabsorbable as well as nonbioabsorbable materials; laser tissue welding; and, ultrasonic bonding. If desired, the layers of the osteogenic osteoimplant can be provided with mechanically interengaging features, e.g., tongue-and-groove, mortise-and-tenon, or dove-tail elements, to facilitate their assembly into the final product and/or to fix the layers to each other in a more secure fashion. The optimal method of assembly would be determined on a case-by-case basis through routine experimentation. In addition to its carrier and osteoinductive layers, the osteoimplant of this embodiment can optionally possess one or more layers formed from one or more other materials or substances.

In another embodiment, the carrier may comprise a single thin sheet of material. The delivery systems thus may comprise a single thin sheet of material coated with osteoinductive factors. The coated sheet of material may be rolled or folded over itself such that the growth factor content in the interior of the sheet approximates the growth factor levels at the surfaces.

VII. Dispersion of Osteoinductive Factors onto Carrier

The osteoinductive factors extracted are combined with the appropriate carrier. Exactly how this occurs can have a significant influence on the biological activity of the final formulation. The extracted osteoinductive factors may have been lyophilized, resulting in a powder composition. In some situations, adding a powder to a bone matrix may be challenging. Thus, it may be desirable to process the osteoinductive factors to form a homogenous mixture that may be more easily added to a carrier. This can have a significant impact on the release kinetics of the growth factor.

Thus, in a specific example, if the osteoinductive factors are lyophilized and then added to a DBM carrier, the solution is likely to be inhomogeneous, with most of the osteoinductive factors concentrated on the outside of the DBM carrier. If the osteoinductive factors are added to a carrier comprising very thin sheets of collagen and the carrier is then folded in on itself, the distribution of growth factor is more homogenous. The collagen sheets in such an embodiment can be very thin, on the order of microns.

Any suitable method for adding, or dispersing, the osteoinductive factors to the carrier may be used. Generally, the procedures used to formulate or disperse osteoinductive factors onto the carrier are sensitive to the physical and chemical state of both the osteoinductive factors and the carrier. The carriers could potentially be added to the extracts in their denatured state, such as in guanidine, allowing the growth factors to be precipitated directly onto the carriers.

In one embodiment, the osteoinductive factors are blended with a bulking agent to form a homogenous mixture. This mixture is added to the carrier.

Alternatively, the osteoinductive factors may be blended with coprecipitates (described more fully above) and this blend may be added to the carrier. For example, the osteoinductive factor and coprecipitate blend may be added to a carrier such as cancellous chips, synthetic calcium phosphate, or a liquid settable polymer. Generally, calcium phosphate is a liquid solid slurry while a polymer is a liquid. Thus, the choice of carrier may depend on the desired characteristics of the composition. Further, a lubricant, such as water, glycerol, or polyethylene glycol may be added.

In an alternative embodiment, the extracted osteoinductive factors may act as their own carrier. In a further embodiment, the above osteoimplant can be combined in various ways with other similar osteoimplants or other materials to form an osteoimplant of laminate-type construction. For example, layers of the osteoimplant of the invention herein can be, through chemical or mechanical means, caused to adhere to each other; or, optionally, with other materials, e.g., reinforcing fibers, fabrics, meshes, etc., between some or all of the osteoimplant layers. Such laminate materials will differ from known osteoimplant laminates such as those disclosed in U.S. Pat. No. 5,899,939, herein incorporated by reference, in that the final size and architecture will be determined by the total amount of starting donor material available rather than the specific size or shape of the usable donor material available.

Formulation

The carrier, the osteoinductive composition, or the osteoimplant may be formulated for a particular use. The formulation may be used to alter the physical, biological, or chemical properties of the carrier. A physician would readily be able to determine the formulation needed for a particular application, taking into account such factors as the type of injury, the site of injury, the patient's health, and the risk of infection. In various embodiments, the osteoinductive composition may comprise, for example less than approximately 0.5% water, less than approximately 1% water, or less than approximately 5% water.

Carriers, osteoinductive compositions, or osteoimplants therefore may be prepared to have selected resorption/loss of osteoinductivity rates, or even to have different rates in different portions of an implant. For example, the formulation process may include the selection of DBM particles of a particular size or composition, combined with the selection of a particular stabilizing agent or agents, and the amounts of such agents.

In one example, it may be desirable to provide an osteoimplant whose osteoinductive factors are active in a relatively constant amount over a given period of time. A DBM carrier comprising factors with longer half-lives can be prepared using a less biodegradable polymer or a larger amount (e.g., a thicker coating) of polymeric compound. Alternatively or additionally, the particle size may be important in determining the half-life of the osteoimplant. In certain embodiments, an inventive formulation may include a mixture of particles, each with a different half-life. Such a mixture could provide the steady or possible unmasking of osteoinductive factors over an extended period of time ranging from days to weeks to months depending on the needs of the injury. Compositions such as this can be formulated to stimulate bone growth in a human patient comparable to the bone growth induced by treatment with 10 µg of rhBMP on a collagen sponge, and preferably comparable to 100 µg, and most preferably 1-10 mg rhBMP. When the degradation of the osteoimplant is of concern, it may be desirable to test the shelf-life of the osteoimplant to determine shelf-life at, for example, 1, 2, or 3 years. This may be done by storing the osteoimplant at, for example, room temperature or, for accelerated testing, 38 degrees Celsius, and periodically checking the inductivity of the osteoimplant. Reference is made to PCT/US05/003092, which is hereby incorporated by reference herein. Implants with enhanced shelf lives may retain more than about 75% and about 80% of their osteoinductivity after as long as, or longer than, three years.

Physical properties such as deformability and viscosity of the carrier may also be chosen depending on the particular clinical application. If DBM is used as a carrier, the particles of the DBM may be mixed with other materials and factors to improve other characteristics of the implant. For example, the improved DBM material may be mixed with other agents to improve wound healing. These agents may include drugs, proteins, peptides, polynucleotides, solvents, chemical compounds, and biological molecules.

Further, the composition may be formulated to be settable and/or injectable. Thus, for example, the composition may be injectable through a 10-gauge, a 12-gauge, or an 18-gauge needle.

Particles of the carrier may also be formed into various shapes and configurations. The particles can be formed into any suitable configuration, including rods, strings, sheets, weaves, solids, cones, discs, fibers, and wedges. In certain embodiments, the shape and size of the particles in the carrier affect the time course of osteoinductivity. For example, in a cone or wedge shape, the tapered end will result in osteoinductivity shortly after implantation of the osteoimplant, whereas the thicker end will lead to osteoinductivity later in the healing process (hours to days to weeks later). In certain embodiments, the particle have a length of greater than 2 mm, greater than 1.5 mm, greater than 1 mm, preferably greater than 500 microns, and most preferably greater than 200 microns across its widest dimension. Also, larger particle size will have induce bone formation over a longer time course than smaller particles. Particles of different characteristics (e.g., composition, size, shape) may be used in the formation of these different shapes and configurations. For example, in a sheet of DBM a layer of long half-life particles may be alternated between layers of shorter half-life particles. See U.S. Pat. No. 5,899,939, herein incorporated by reference, for suitable examples. In a weave, strands composed of short half-life particles may be woven together with strands of longer half-lives.

In one embodiment, fibrous DBM is shaped into a matrix form carrier as described in U.S. Pat. No. 5,507,813, herein incorporated by reference. The shaped DBM is then embedded within a diffusion barrier type matrix, such that a portion of the matrix is left exposed free of the matrix material. Particularly preferred blocking matrices are starch, phosphatidyl choline, tyrosine polycarbonates, tyrosine polyarylates, polylactides, polygalactides, or other resorbable polymers or copolymers. Devices prepared in this way from these matrices have a combination of immediate and longer lasting osteoinductive properties and are particularly useful in promoting bone mass formation in human posterolateral spine fusion indications.

In another embodiment, carriers having a pre-selected three-dimensional shape are prepared by repeated application of individual layers of DBM, for example by 3-D printing as described by U.S. Pat. Nos. 5,490,962, 5,518,680, and 5,807,437, each incorporated herein by reference. Different layers may comprise individual stabilized DBM preparations, or alternatively may comprise DBM layers treated with stabilizing agents after deposition of multiple layers.

In the process of preparing the osteoimplant, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing DBM such as defatting, sonication, and lyophilization may also be used in preparing a DBM carrier. Since the biological activity of demineralized bone is known to be detrimentally affected by most terminal sterilization processes, care must be taken when sterilizing the inventive compositions.

VIII. Optional Additives

Optionally, other additives may be included in the osteoinductive bone matrix. It will be appreciated that the amount of additive used will vary depending upon the type of additive, the specific activity of the particular additive preparation employed, and the intended use of the composition. The desired amount is readily determinable by the user. Any of a variety of medically and/or surgically useful optional substances can be incorporated in, or associated with, the osteoinductive factors either before, during, or after preparation of the osteogenic composition.

In certain embodiments, the additive is adsorbed to or otherwise associated with the osteoimplant. The additive may be associated with the osteoimplant through specific or nonspecific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the osteoimplant, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoimplant. An additive may be provided within the osteoimplant in a sustained release format. For example, the additive may be encapsulated within biodegradable nanospheres, microspheres, etc.

It will be understood by those skilled in the art that the lists of optional substances herewith included are not intended to be exhaustive and that other materials may be admixed with bone-derived elements within the practice of the present invention.

Radiopaque Substances

Radiopaque substances may be added to impart radiopacity to the composition. Examples of substances imparting radiopacity include for example, fully mineralized bone particles, Barium and Iodine containing compounds or compositions, e.g., Barium Sulfate and Barium Sulfate for Suspension, Iopanoic Acid, and the like. When employed, substances imparting radiopacity will typically represent from about 1 to about 25 weight percent of the bone particle containing composition, calculated prior to forming the shaped material.

Angiogenesis Promoting Materials

Development of a vasculature around the implant site may also be important to forming new bone and/or cartilage tissues. Angiogenesis may be an important contributing factor for the replacement of new bone and cartilage tissues. In certain embodiments, angiogenesis is promoted so that blood vessels are formed at the site to allow efficient transport of oxygen and other nutrients and growth factors to the developing bone or cartilage tissue. Thus, angiogenesis promoting factors may be included in the osteoimplant to increase angiogenesis in that region. For example, class 3 semaphorins, e.g., SEMA3, controls vascular morphogenesis by inhibiting integrin function in the vascular system, Serini et al., *Nature*, (July 2003) 424:391-397, incorporated herein by reference, and may be included in the osteoimplant.

Bioactive Agents

The osteoconductive composition may provide a system for delivering bioactive agents, such as osteoinductive factors, to a host animal. Thus, the osteoimplant enables an improved healing response to the implant without the need to administer separately the bioactive agent. A problem with the introduction of the bioactive agent at the site is that it is often diluted and redistributed during the healing process by the circulatory systems (e.g., blood, lymph) of the recipient before complete healing has occurred. A solution to this problem of redistribution is to affix the bioactive components to the osteoimplant. Some preferred bioactive agents that can be delivered using a DBM composition include agents that promote the natural healing process, i.e., resorption, vascularization, angiogenesis, new growth, etc. In one embodiment, the osteoimplant is provided in which DBM, together with a stabilizing agent, is used to deliver the biologically active agent. It is expected that the stabilizing agent will protect the biologically active agent from degradation, and therefore will extend its active life after delivery into the recipient animal. In certain embodiments, the bioactive agent is an osteoinductive agent, and in certain embodiments, the DBM may be used to deliver more than one bioactive agent, preferably more than two, and more preferably sometimes more than three bioactive agents. The bioactive agent may be associated with the DBM. For example, the bioactive agent may be associated with the DBM through electrostatic interactions, hydrogen bonding, pi stacking, hydrophobic interactions, van der Waals interactions, etc. In certain embodiments, the bioactive agent is attached to the DBM through specific interactions such as those between a receptor and its ligand or between an antibody and its antigen. In other embodiments, the bioactive agent is attached to the DBM through non-specific interactions (e.g., hydrophobic interactions).

Medically/surgically useful substances include physiologically or pharmacologically active substances that act locally or systemically in the host. Generally, these substances may include bioactive substances which can be readily incorporated into the osteoimplant and include, e.g., demineralized bone powder as described in U.S. Pat. No. 5,073,373, the contents of which are incorporated herein by reference; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation.

In certain embodiments, the agent to be delivered is adsorbed to or otherwise associated with the osteoimplant. The agent may be associated with the osteoimplant through specific or non-specific interactions; or covalent or noncovalent interactions. Examples of specific interactions include those between a ligand and a receptor, a epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent is attached to the osteoimplant using a linker so that the agent is free to associate with its receptor or site of action in vivo. In certain embodiments, the agent to be delivered may be attached to a chemical compound such as a peptide that is recognized by the matrix of the DBM composition. In another embodiment, the agent to be delivered is attached to an antibody, or fragment thereof, that recognizes an epitope found within the matrix of the DBM composition. In a further embodiment, the agent is a BMP, TGF-β, IGF, parathyroid hormone (PTH), growth factors, or angiogenic factors. In certain embodiments at least two bioactive agents are attached to the DBM composition. In other embodiments at least three bioactive agents are attached to the DBM composition.

Osteoinducing Agents

Other osteoinducing agents besides the extracted osteoinductive factors may be added to the carrier. These agents may be added in an activated or non-activated form. These agents may be added at anytime during the preparation of the inventive material. For example, in the case of a DBM carrier, the osteoinducing agent may be added after the demineralization step and prior to the addition of the stabilizing agents so that the added osteoinducing agent is protected from exogenous degrading enzymes once implanted. In some embodiments the DBM is lyophilized in a solution containing the osteoinducing agent. In certain other embodiments, the osteoinducing agents are adhered onto the hydrated demineralized bone matrix and are not freely soluble. In other instances, the osteoinducing agent is added after addition of a stabilizing agent so that the osteoinducing agent is available immediately upon implantation of the DBM.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Suitable osteoinducing agents include bone morphogenic proteins (BMPs), transforming growth factor (TGF-0), insulin-like growth factor (IGF-1), parathyroid hormone (PTH), and angiogenic factors such as VEGF. In one embodiment, the inducing agent is genetically engineered to comprise an amino acid sequence which promotes the binding of the inducing agent to the DBM or the carrier. Sebald et al., PCT/EPOO/00637, incorporated herein by reference, describe the production of exemplary engineered growth factors suitable for use with DBM.

VIII. Treatment of Compositions

In the process of preparing improved inventive bone and cartilage matrix materials, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing bone and cartilage matrices, such as defatting, sonication, and lyophilization may also be used in preparing the carrier. Since the biological activity of various materials including demineralized bone is known to be detrimentally affected by most terminal sterilization processes, care must be taken when sterilizing the inventive compositions. In some embodiments, the osteoimplants described herein will be prepared aseptically or sterilized.

IX. Example Compositions

In one embodiment, the osteoimplant comprises a combination of DBM and osteoinductive factors from bone that has 2 to 150 fold greater activity than DBM that has not been supplemented, as measured by the ability of the composition to induce heterotopic bone formation in a rat or mouse. Various ratios of DBM to osteoinductive factors may be used, ranging from 1 gram DBM: 1 ug osteoinductive factors to 1 gram DBM: 100 mg osteoinductive factors. The osteoimplant may comprise osteoinductive growth factors extracted from DBM or recovered from acid baths used for demineralization of bone matrix and demineralized bone matrix and may exhibit the ability to induce specific alkaline phosphatase activity higher than those of standard demineralized bone matrix preparations, for example, 2 to 100,000,000 higher than standard dermineralized bone matrix preparations in cultured C2C12.

In another embodiment, the osteoimplant comprises a combination of DBM, osteoinductive factors, and a carrier in various ratios. Any suitable carrier may be used, including polyethylene glycol, lecithin, starch, collagen, hydroxyapatite, or hyalurounic acid. Suitable ratios include 1 gram DBM: 10 ug to 100 mg osteoinductive factors: 100 mg to 10 grams carrier.

In a further embodiment, the osteoimplant comprises a combination of nondemineralized bone with osteoinductive factors from bone that has the ability to induce posterolateral spine fusion in higher animals, such as humans and dogs, without the addition of recombinant growth factors or iliac crest autograft. Various ratios of bone to osteoinductive factors ranging from 1 gram bone: 1 ug osteoinductive factors to 1 gram bone: 100 mg osteoinductive factors can be used.

In yet a further embodiment, the osteoimplant comprises a combination of mineralized bone, osteoinductive factors, and a carrier in various ratios. Any suitable carrier may be used, as set forth above. Suitable ratios include 1 gram DBM: 10 ug to 100 mg osteoinductive factors: 100 mg to 10 grams carrier, with the ability to induce posterolateral spine fusion in humans or dogs without the addition of recombinant growth factors or iliac crest autograft.

As previously described, in another embodiment, an osteoinductive material comprising a mineralized particulated material, osteoinductive growth factors, and a demineralized bone matrix scaffold is provided.

In a further previously described embodiment, an osteoinductive composition comprising noncollagenous proteins extracted from demineralized bone or recovered from acid used to demineralize bone and mineral recovered acid used to demineralize bone. Alternatively, the osteoinductive composition may comprise noncollagenous proteins extracted from demineralized bone or recovered from acid used to demineralize bone and a demineralized bone matrix scaffold.

In yet a further previously described emobidment, an osteoinductive composition comprising mineralized or surface demineralized bone particles and extracts of DBM may be provided.

X. Assessment of Osteogenic Activity

Induction of bone formation can be determined by a histological evaluation showing the de novo formation of bone with accompanying osteoblasts, osteoclasts, and osteoid matrix. For example, osteoinductive activity of an osteoinductive factor can be demonstrated by a test using a substrate onto which material to be tested is deposited. The substrate with deposited material is implanted subcutaneously in a test animal. The implant is subsequently removed and examined microscopically for the presence of bone formation including the presence of osteoblasts, osteoclasts, and osteoid matrix. A suitable procedure for assessing osteoinductive activity is illustrated in Example 5 of U.S. Pat. No. 5,290,763, herein incorporated by reference. Although there is no generally accepted scale of evaluating the degree of osteogenic activity, certain factors are widely recognized as indicating bone formation. Such factors are referenced in the scale of 0-8 which is provided in Table 3 of example 1 of U.S. Pat. No. 5,563, 124, herein incorporated by reference. The 0-4 portion of this scale corresponds to the scoring system described in U.S. Pat. No. 5,290,763, which is limited to scores of 0-4. The remaining portion of the scale, scores 5-8, references additional levels of maturation of bone formation. The expanded scale also includes consideration of resorption of collagen, a factor which is not described in the '763 patent.

In studies, a typical amount of DBM for implantation is 20 mg in a mouse and 40 mg in a rat. Significant increases in the growth factor dose, for example, 150× dose (or 150 times the growth factor found in normal DBM), lead to significantly more and potentially faster bone growth with larger volume bone growth, more dense bone growth, larger nodules of bone growth, higher x-ray density, and, generally, a higher osteoinductive score. Associated with this increase in osteoinductivity can be a cortical shell surrounding the nodule and some level of vascularization in the nodule. However, the ability to quantitatively measure is generally limited by the method used, and generally measured increases in osteoinductive activity are not linear with the increase in dosage. Thus, if 20 mg of DBM gives an osteoinductive activity of 1, 100 times the growth factor dose (2000 mg of DBM growth factors) does not give an osteoinductive activity of 100. Instead, it may result in an osteoinductive activity of about 20. A limitation of measurement using osteoinductive scores is that, in some situations, the system's ability to respond may be saturated. Thus, for example, if the score ranges only from 1 to 4, two samples may have the same score (4) but may not, in fact, be comparable. This is particularly the case when the bone resulting from one method or implant is qualitatively better than the bone resulting from another method or implant. That is, both methods or implants may result in an osteoinductive score of 4 but one may result in qualitatively better bone than the other. Thus, in some situations it may be desirable to test speed of growth, density, presence of cortical bone, shelling, and/or other factors showing an increase over normal demineralized bone matrix. Further, in addition to, or in lieu of, testing at 28 days, it may be desirable to test inductivity at 21 days Generally, inductivity may be measured histomorphometrically by methods known in art.

Further, delivering 100 times the growth factor dose may be challenging. In filling a bone defect, only as much filler may be used as there is bone void space.

XI. Uses

Therapeutic Uses

The osteogenic osteoimplant is intended to be applied at a bone repair site, for example, a site resulting from injury, defect brought about during the course of surgery, infection, malignancy, or developmental malformation. The osteoimplant can be utilized in a wide variety of orthopedic, periodontal, neurosurgical, and oral and maxillofacial surgical procedures.

At the time just prior to when the osteoimplant of the invention is to be placed in a defect site, optional materials, e.g., autograft bone marrow aspirate, autograft bone, preparations of selected autograft cells, autograft cells containing genes encoding bone promoting action, etc., can be combined with the osteoimplant. The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

The osteoinductive compositions may also be used as drug delivery devices. In certain embodiments, association with the osteoinductive compositions increases the half-life of the relevant biologically active agent(s). Particularly preferred inventive drug delivery devices are used to deliver osteoinductive growth factors. Other preferred agents to be delivered include factors or agents that promote wound healing. However, the osteoinductive compositions may alternatively or additionally be used to deliver other pharmaceutical agents including antibiotics, anti-neoplastic agents, growth factors, hematopoietic factors, nutrients, an other bioactive agents described above. The amount of the bioactive agent included with the DBM composition can vary widely and will depend on such factors as the agent being delivered, the site of administration, and the patient's physiological condition. The optimum levels is determined in a specific case based upon the intended use of the implant.

Non-Therapeutic Uses

In addition to therapeutic uses involving implantation into a subject, the osteoinductive compositions have a number of other uses. For example, they can be used to generate cell lines, tissues, or organs having osteogenic or chondrogenic properties. In particular, cells can be removed from a donor and cultured in the presence of an osteoinductive composition. The invention includes such cells as well as tissues and organs derived therefrom. The cells, tissues, or organs may be implanted into the original donor after a period of culture in vitro or may be implanted into a different subject.

XII. Conclusion

In certain embodiments, the osteoinductive compositions and associated osteoimplants produce bone or cartilage in an animal model and/or in human patients with similar timing and at a level at least 10%, 20%, 35%, 50%, 100%, 200%, 300%, or 400% or greater osteogenic, osteoinductive or chondrogenic activity than a corollary carrier that has not been exposed to a treatment or condition as described herein. Of course, one skilled in the art will appreciate that these values may vary slightly depending on the type of test used to measure the osteoinductivity or osteogenic or chondrogenic activity described above. The test results may fall within the range of 10% to 35%, 35% to 50%, 50% to 100%, 100% to 200%, and 200% to 400%. In certain embodiments, when an osteoimplant is implanted into a bone defect site, the osteoimplant has an osteoinductivity score of at least 1, 2, 3, or 4 in an animal model and/or in humans.

Although the invention has been described with reference to preferred embodiments, persons skilled in the art will recognize that changes may be made in form and detail without departing from the spirit and scope of the invention.

The invention claimed is:

1. A method for producing an osteogenic growth factor composition comprising:
   providing bone;
   demineralizing the bone in an acid solution to produce a demineralized bone material and a mineral recovered acid;
   extracting osteogenic growth factors from the demineralized bone material; and
   combining the osteogenic growth factors extracted from the demineralized bone material and the mineral recovered acid to produce the osteogenic growth factor composition.

2. The method of claim 1, further comprising purifying the osteogenic growth factors prior to the combining step.

3. The method of claim 2, wherein purifying the growth factors comprises purifying by chromatography.

4. The method of claim 2, wherein purifying the osteogenic growth factors comprises purifying by electrophoresis.

5. The method of claim 1, wherein the step of extracting osteogenic growth factors from the demineralized bone occurs in the presence of one or more extractant or one or more chemical chaperone to produce non-denatured growth factors.

6. The method of claim 5, wherein the one or more chemical chaperone is chosen from the group consisting of glycerol, trehalose, proline, glycine, betaine, and dextrose.

7. The method of claim 5, wherein the one or more extractant is chosen from the group consisting of guanidine hydrochloride, urea, citric acid, and hydrochloric acid.

* * * * *